(12) United States Patent
Moorman et al.

(10) Patent No.: US 11,733,217 B1
(45) Date of Patent: Aug. 22, 2023

(54) METHODS AND SYSTEMS FOR OPIOID DETECTION

(71) Applicant: National Technology & Engineering Solutions of Sandia, LLC, Albuquerque, NM (US)

(72) Inventors: Matthew W. Moorman, Albuquerque, NM (US); Joshua J. Whiting, Albuquerque, NM (US); Curtis D. Mowry, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 370 days.

(21) Appl. No.: 16/984,923

(22) Filed: Aug. 4, 2020

Related U.S. Application Data

(60) Provisional application No. 62/905,871, filed on Sep. 25, 2019.

(51) Int. Cl.
| | | |
|---|---|---|
| *G01N 30/60* | (2006.01) | |
| *G01N 30/76* | (2006.01) | |
| *G01N 30/06* | (2006.01) | |
| *G01N 27/622* | (2021.01) | |
| *B01J 20/281* | (2006.01) | |
| *G01N 30/00* | (2006.01) | |
| *G01N 30/02* | (2006.01) | |

(52) U.S. Cl.
CPC ....... *G01N 30/6095* (2013.01); *G01N 27/622* (2013.01); *G01N 30/06* (2013.01); *G01N 30/482* (2013.01); *G01N 30/76* (2013.01); *G01N 2030/025* (2013.01); *G01N 2030/484* (2013.01)

(58) Field of Classification Search
CPC .. G01N 30/6095; G01N 27/622; G01N 30/06; G01N 30/482; G01N 30/76; G01N 2030/025; G01N 2030/484
See application file for complete search history.

(56) References Cited

U.S. PATENT DOCUMENTS

| | | |
|---|---|---|
| 5,820,922 A | 10/1998 | Ricco et al. |
| 5,834,627 A | 11/1998 | Ricco et al. |
| 6,068,684 A | 5/2000 | Overton |
| 6,171,378 B1 | 1/2001 | Manginell et al. |
| 6,527,835 B1 | 3/2003 | Manginell et al. |
| 6,666,907 B1 | 12/2003 | Manginell et al. |
| 6,669,392 B2 | 12/2003 | Bora |
| 6,786,719 B2 | 9/2004 | Gardner et al. |
| 7,078,237 B1 | 7/2006 | Mowry et al. |
| 7,168,298 B1 | 1/2007 | Manginell et al. |
| 7,422,724 B1 | 9/2008 | Manginell et al. |
| 7,727,315 B2 | 6/2010 | Manginell et al. |

(Continued)

OTHER PUBLICATIONS

U.S. Appl. No. 10/035,537, filed Oct. 23, 2001, Mowry et al.

(Continued)

*Primary Examiner* — Jennifer Wecker
*Assistant Examiner* — Michael Paul Shimek
(74) *Attorney, Agent, or Firm* — Madelynne J. Farber; Samantha Updegraff; Fish & Richardson, P. C.

(57) ABSTRACT

The present invention relates to detection systems for detecting an opioid compound by use of pyrolysis, as well as methods thereof. In particular, the systems are configured to detect the presence of a backbone fragment indicative of a class of opioid compounds, including opioid analogues.

8 Claims, 5 Drawing Sheets

Synthetic Opioid Pyrolysis

"Backbone" pyrolysis fragment independent of analog chemistry

Micro Gas Chromatograph (μGC)

Deployable Synthetic Opioid Detector

Sandia's Miniature Ion Mobility Spectrometer (IMS)

(56) References Cited

U.S. PATENT DOCUMENTS

| | | |
|---|---|---|
| 8,298,488 B1 | 10/2012 | Lewis et al. |
| 10,261,048 B2 | 4/2019 | Davis et al. |
| 2009/0223310 A1* | 9/2009 | Syage .................. G01N 1/2205 73/863.23 |
| 2012/0103061 A1* | 5/2012 | Nacson .............. G01N 33/0004 250/336.1 |

OTHER PUBLICATIONS

U.S. Appl. No. 11/120,877, filed May 3, 2005, Manginell et al.
U.S. Appl. No. 11/656,120, filed Jan. 22, 2007, Manginell et al.
U.S. Appl. No. 11/656,129, filed Jan. 22, 2007, Manginell et al.
U.S. Appl. No. 60/358,250, filed Feb. 19, 2002, Gardner et al.
U.S. Appl. No. 60/763,736, filed Jan. 31, 2006, Manginell et al.
U.S. Appl. No. 60/763,755, filed Jan. 31, 2006, Manginell et al.
U.S. Appl. No. 60/773,863, filed Feb. 16, 2006, Manginell et al.
U.S. Appl. No. 62/016,786, filed Jun. 25, 2014, Robinson et al.
Adkins, D. et al., "Advanced Detectors for Chemical Weapon Detection," Sandia National Laboratories, SAND2003-3810A, 1 page.
Adkins, D. et al., "Advanced Detectors for Chemical Weapon Detection," $2^{nd}$ Joint Conf. on Point Detection for Chemical and Biological Defense (2004) SAND2004-0887C, 7 pages.
Allen, A. et al., "Calorimetry and Mass Analysis of Polymers Utilizing Sandia Microfabricated Devices for Aging, Heating, and Sample Preparation," Sandia National Laboratories, SAND2011-7357P, 1 page.
Allen, A. et al., "Microfabricated Temperature Controlled Sample Treatment Platform for Improving Mass Spectrometry of Polymers," Sandia National Laboratories, SAND2012-9148P, 1 page.
Breindahl, T. et al., Identification of a new psychoactive substance in seized material: the synthetic opioid N-phenyl-N-[1-(2-phenethyl)piperidin-4-yl]prop-2-enamide (Acrylfentanyl), Drug Testing and Analysis (2016) 9:415-422.
Brocato, T. A. et al., "Investigations into the chemical structure based selectivity of the microfabricated nitrogen-phosphorus detector," Sensors and Actuators B: Chemical (2016) 224:618-623, SAND2015-10395J.
Casalnuovo, S. A. et al., "Gas Phase Chemical Detection with an Integrated Chemical Analysis System," 1999 Joint Meeting EFTF-IEEE IFCS, pp. 991-996.
Cruz, D. et al., "Geometrically optimized thermal conductivity detector for chemical sensing," Sandia National Laboratories, SAND2002-0685A, 1 page.
Cruz, D. et al., "Microfabricated thermal conductivity detector for the micro-ChemLab™," Sensors and Actuators B (2007) 121:414-422.
Chemical and Biological Sensor Standards Study, DARPA, Arlington, VA (2005) 37 pages.
Frye-Mason, G. et al., "Hand-Held Miniature Chemical Analysis System (μChemLab) for Detection of Trace Concentrations of Gas Phase Analytes," Sandia National Laboratories, SAND2000-1480A, 4 pages.
Frye-Mason, G. et al., Expanding the Capabilities and Applications of Gas Phase Miniature Chemical Analysis Systems (μChemLab™), Sandia National Laboratories, SAND2001-3230A, 3 pages.
Frye-Mason, G. et al., "Microfabricated Gas Phase Chemical Analysis Systems," Digest of Papers for "Microprocesses and Nanotechnology '99" held on Jul. 6-8, 1999 in Yokohama, Japan, 2 pages.
Garg, A. et al., "Forced degradation of fentanyl: Identification and analysis of impurities and degradants," Journal of Pharmaceutical and Biomedical Analysis (2010) 53:325-334.
Grate, J. W., "Acoustic Wave Microsensor Arrays for Vapor Sensing," Chem. Rev. (2000) 100:2627-2648.
Havey, C. D. et al., "Evaluation of a micro-fabricated pyrolyzer for the detection of *Bacillus anthracis* spores," J. Anal. Appl. Pyrolysis (2004) 72:55-61.
Hess, R., "Detection of toxic compounds using a microfabricated thin film nitrogen-phosphorus thermionic detector," Sandia National Laboratories, SAND2012-2445C, 15 pages.
2013 HPC Annual Report, Sandia Mission Computing, Sandia National Laboratories, Jennings, B. (ed.), 40 pages.
Hudson, M. L. et al., "Design, Testing, and Simulation of Microscale Gas Chromatography Columns," Sandia National Laboratories, SAND1998-1551C, 10 pages.
Johnson, R. S. et al., "Thermally-activated Pentanol Delivery from Precursor Poly(*p*-phenylenevinylene)s for MEMS Lubrication," Sandia National Laboratories, SAND2012-3168J, 16 pages.
Kottenstette, R. et al., "Development and Testing of Sandia's CWA Point Detector Technology," Sandia National Laboratories, SAND2004-1076C, 7 pages.
Lewis, P. R. et al., "Recent Advancements in the Gas-Phase MicroChemLab," IEEE Sensors Journal (2006) 6(3):784-795.
Manginell, R. P. et al., "Two-Dimensional Modeling and Simulation of Mass Transport in Microfabricated Preconcentrators," IEEE Sensors Journal (2007) 7(7):1032-1041.
Manginell, R. P. et al., "Mass-Sensitive Microfabricated Chemical Preconcentrator," Journal of Microelectromechanical Systems (2008) 17(6):1396-1407.
Manginell, R. P. et al., "Microfabrication of Membrane-Based Devices by Deep-Reactive Ion Etching (DRIE) of Silicon," Sandia National Laboratories, SAND1998-1778C, 10 pages.
Manginell, R. P. et al., "Finite Element Modeling of a Microhotplate of Microfluidic Applications," Sandia National Laboratories, SANS1999-0576C, 4 pages.
Manginell, R. P. et al., "Microfabricated Planar Preconcetrator," Sandia National Laboratories, SAND2000-0820C, 4 pages.
Manginell, R. P. et al., "Monolithically-Integrated MicroChemLab™ for Gas-Phase Chemical Analysis," $7^{th}$ International Conference on Miniaturized Chemical and Biochemical Analysis Systems, Oct. 5-9, 2003, Squaw Valley, CA, pp. 1247-1250.
Manginell, R. P. et al., "A Monolithically-Integrated mGC Chemical Sensor System," Sensors (2011) 11:6517-6532.
Manral, L. et al., "Thermal Behaviour of Fentanyl and its Analogues During Flash Pyrolysis," Journal of Thermal Analysis and Calorimetry (2009) 96(2):531-534.
Map of Significant Fentanyl Seizures of More than 1 Kilogram, Jan. 2016-Jun. 2017, DEA field division investigative reporting, 1 page.
Martin, S. J. et al., "Gas Sensing with Acoustic Devices," IEEE Ultrasonics Symposium (1996) pp. 423-434.
Martin, S. T. et al., "Magnetically-Excited Flexural Plate Wave Resonator," IEEE Transactions on Ultrasonics, Ferroelectrics, and Frequency Control (1998) 45(5):1381-1387.
Matzke, C. M. et al., "Microfabricated silicon gas chromatographic microchannels: fabrication and performance," Proceedings of SPIE 3511, Micromachining and Microfabrication Process Technology IV (1998) Santa Clara, CA, pp. 262-268.
Morgan, C. H. et al., "Rapid identification of bacteria with miniaturized pyrolysis/GC analysis," Proceedings of SPIE vol. 4205 (2001) Advanced Environmental and Chemical Sensing Technology, Vo-Dinh, T et al., (eds.) pp. 199-206.
Morgan, C. H. et al., "Rapid Identification of Bacteria with Miniaturized Pyrolysis/GC Analysis," Sandia National Laboratories, SAND2000-1238P, 17 pages.
MX908 Drug Hunter Overview, 908devices, Boston, MA, 2 pages.
Nishikawa, R. K. et al., "Potential Biomarkers of Smoked Fentanyl Utilizing Pyrolysis Gas Chromatography-Mass Spectrometry," Journal of Analytical Toxicology (2009) 33:418-422.
Park, J. et al., "Vapor Recognition with Small Arrays of Polymer-Coated Microsensors. A Comprehensive Analysis," Anal. Chem. (1999) 71:3877-3886.
Paxton, W. F. et al., "Toward Polymer-coated Si Nanowire FETs for Robust Biosensors," Sandia National Laboratories, SAND2017-11771c, 1 page.
Pfeifer, K. B. et al., "Measurement of Ion Swarm Distribution Functions in Miniature Low-Temperature Co-Fired Ceramic Ion Mobility Spectrometer Drift Tubes," Anal. Chem. (2005) 77:5215-5220.

(56) References Cited

OTHER PUBLICATIONS

Pfeifer, K. B. et al., "Signal-to-Noise and Resolution Enhancement in Ion Mobility Spectrometry Using Correlation Gating Techniques: Barker Codes," IEEE Sensors Journal (2007) 7(8):1130-1137.

Regmi, B. P. et al., "Micro Gas Chromatography: An Overview of Critical Components and Their Integration," Anal. Chem. (2018) 90:13133-13150.

Schwindt, P. D. D. et al., "A highly miniaturized vacuum package for a trapped ion atomic clock," Review of Scientific Instruments (2016) 87, 053112, 9 pages.

Simonson, R. J. et al., "Microfabricated Nitrogen-Phosphorus Detector: Chemically Mediated Thermionic Emission," Sandia National Laboratories, SAND2012-7778, 51 pages.

Skulska, A. et al., "Fentanyl and its Analogues in the Forensic Laboratory. Medical and Analytical Problems," Z Zagadnien Nauk Sadowych (2004) 59:127-142.

Smiths Detection Group Ltd., "Five Common Risk Scenarios First Responders Face when Coming in Contact with Illicit Opioids," 2018, 3 pages.

Smiths Detection Group Ltd., "Fentanyl: What are the exposure risks?" 2018, 2 pages.

Terry, S. C. et al., "A Gas Chromatographic Air Analyzer Fabricated on a Silicon Wafer," IEEE Transactions on Electron Devices (1979) 26(12):1880-1886.

Tian, W.-C. et al., "Microfabricated Preconcentrator-Focuser for a Microscale Gas Chromatograph," Journal of Microelectromechanical Systems (2003) 12(3):264-272.

U.S. Department of Justice, Drug Enforcement Administration, "Fentanyl A Briefing Guide for First Responders," 20 pages.

Valdez, C. A. et al., "Analysis of chemical warfare agents by gas chromatography-mass spectrometry: methods for their direct detection and derivatization approaches for the analysis of their degradation products," Reviews in Analytical Chemistry (2017) 37(1), 26 pages.

Vandergrift, G. W. et al., "Paper spray mass spectrometry for the direct, semi-quantitative measurement of fentanyl and norfentanyl in complex matrices," Clinical Biochemistry (2018) 54:106-111.

Verkouteren, J. R. et al., "Reliability of ion mobility spectrometry for qualitative analysis of complex, multicomponent illicit drug samples," Forensic Science International (2011) 206:190-196.

Wang, D. et al., "Sol-Gel Column Technology for Single-Step Deactivation, Coating, and Stationary-Phase Immobilization in High-Resolution Capillary Gas Chromatography," Anal. Chem. (1997) 69:4566-4576.

Washburn, C. et al., "Micro-Flame Ionization Detection Using a Catalytic Micro-Combustor," Solid State Chemical Sensing at High Temperatures IEEE Sensors (2005) Irvine, CA, SAND2005-7405P, 19 pages.

Whiting, J. J. et al., "μChemLab™—Twenty Years of Developing CBRNE Detection Systems with Low False Alarm Rates," Chemical, Biological, Radiological, Nuclear, and Explosives (CBRNE) Sensing XX, Proc. of SPIE vol. 11010, 1101012, Guicheteau, J. A. et al., (eds.), 13 pages.

Whiting, J. J. et al., "A Hydrogen Bonded Acidic Polymer (DKAP) as a Gas Chromatography Stationary Phase for Organophosphonates and Organophosphates," Sandia National Laboratories, SAND2019-7658C, 1 page.

Whiting, J. J. et al., "μChemLab™—Twenty Years of Developing CBRNE Detection Systems with Low False Alarm Rates," Sandia National Laboratories, SAND2019-7659C, 13 pages.

Whiting, J. J. et al., "μChemLab™—Twenty Years of Developing CBRNE Detection Systems with Low False Alarm Rates," Sandia National Laboratories, SAND2016-7661C, 41 pages.

Whiting, J. J. et al., "High-Speed Two-Dimensional Gas Chromatography Using Microfabricated GC Columns Combined with Nanoelectromechanical Mass Sensors," Transducers (2009) Denver, CO, Jun. 21-25, pp. 1666-1669.

Whiting, J. J. et al., "A high-speed, high-performance, microfabricated comprehensive two-dimensional gas chromatograph," Lab Chip (2019) 19:1633-1643.

\* cited by examiner

METHODS AND SYSTEMS FOR OPIOID DETECTION

CROSS-REFERENCE TO RELATED APPLICATIONS

This application claims priority to U.S. Provisional Patent Application No. 62/905,871, filed on Sep. 25, 2019, and entitled "METHODS AND SYSTEMS FOR OPIOID DETECTION", the entirety of which is incorporated herein by reference for any purpose.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to detection systems for detecting an opioid compound by use of pyrolysis, as well as methods thereof. In particular, the systems are configured to detect the presence of a backbone fragment indicative of a class of opioid compounds, including opioid analogues.

BACKGROUND OF THE INVENTION

Synthetic opioids, e.g., fentanyl and its analogues, are a toxic drug class that readily cause harm and present detection challenges. In particular, rapidly proliferating, altered chemical structures can provide increased drug potency, while circumventing detection. Literature reports approximately thousands of possible fentanyl analogues, but only about hundreds of specific formulations have been reported or studied. Most commercial detector technologies are capable of reporting only a few (e.g., tens) of those. Accordingly, there is a need for novel detection approaches that are independent of a drug's chemical structure, yet capable of reporting the presence of a synthetic opioid.

SUMMARY OF THE INVENTION

We aim to significantly simplify the synthetic opioid detection challenge by using a unique pyrolysis-based detection method that is amenable to portable instrumentation. In particular, pyrolysis can be employed to produce one or more "backbone" chemical fragments that are signatures of fentanyl or an analogue thereof. Furthermore, secondary fragment(s) can provide additional chemical information useful for identification. The "backbone" fragment represents an opportunity to detect synthetic opioid compounds independent of their analogue.

To promote portable detection, such synthetic opioid pyrolysis fragments can be detected with a miniaturized ion-mobility spectrometer (IMS) or mass spectrometer (MS) detector.

Furthermore, pyrolysis can also be conducted using a miniaturized pyrolyzer. Such a combination could provide a portable sensor architecture capable of native detection of thousands of possible opioid compounds with a low false alarm rate. Additional details follow.

Definitions

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "micro" is meant having at least one dimension that is less than 1 mm and, optionally, equal to or larger than about 1 μm. For instance, a microstructure (e.g., any structure described herein) can have a length, width, height, cross-sectional dimension, circumference, radius (e.g., external or internal radius), or diameter that is less than 1 mm.

By "nano" is meant having at least one dimension that is less than 1 m but equal to or larger than about 1 nm. For instance, a nanostructure (e.g., any structure described herein, such as a nanoparticle) can have a length, width, height, cross-sectional dimension, circumference, radius (e.g., external or internal radius), or diameter that is less than 1 μm but equal to or larger than 1 nm. In other instances, the nanostructure has a dimension that is of from about 1 nm to about 1 μm.

As used herein, the terms "top," "bottom," "upper," "lower," "above," and "below" are used to provide a relative relationship between structures. The use of these terms does not indicate or require that a particular structure must be located at a particular location in the apparatus.

The term "acyl," or "alkanoyl," as used interchangeably herein, represent an alkyl group, as defined herein, or hydrogen attached to the parent molecular group through a carbonyl group, as defined herein. This group is exemplified by formyl, acetyl, propionyl, butanoyl, and the like. The alkanoyl group can be substituted or unsubstituted. For example, the alkanoyl group can be substituted with one or more substitution groups, as described herein for alkyl. In some embodiments, the unsubstituted acyl group is a $C_{2-7}$ acyl or alkanoyl group.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons ($C_{7-16}$ alkaryl), as well as those having an alkylene group with 1 to 6 carbons and an aryl group with 4 to 18 carbons (i.e., $C_{1-6}$ alk-$C_{4-18}$ aryl).

By "alkcycloalkyl" is meant a cycloalkyl group, as defined herein, attached to the parent molecular group through an alkylene group, as defined herein. The alkcycloalkyl group can be substituted or unsubstituted. For example, the alkcycloalkyl group can be substituted with one or more substitution groups, as described herein for alkyl.

By "alkenyl" is meant an optionally substituted $C_{2-24}$ alkyl group having one or more double bonds. The alkenyl group can be cyclic (e.g., $C_{3-24}$ cycloalkenyl) or acyclic. The alkenyl group can also be substituted or unsubstituted. For example, the alkenyl group can be substituted with one or more substitution groups, as described herein for alkyl.

By "alkenylene" is meant a multivalent (e.g., bivalent, trivalent, tetravalent, etc.) form of an alkenyl group, as described herein. In some embodiments, the alkenylene group is a $C_{2-3}$, $C_{2-6}$, $C_{2-12}$, $C_{2-16}$, $C_{2-18}$, $C_{2-20}$, or $C_{2-24}$ alkylene group. The alkenylene group can be branched or unbranched.

The alkenylene group can also be substituted or unsubstituted. For example, the alkenylene group can be substituted with one or more substitution groups, as described herein for alkyl.

By "alkheterocyclyl" represents a heterocyclyl group, as defined herein, attached to the parent molecular group through an alkylene group, as defined herein. Exemplary unsubstituted alkheterocyclyl groups are of from 2 to 14 carbons.

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can be substituted or unsubstituted. For example, the alkoxy group can be substituted with one or more substitution groups, as described herein for alkyl. Exemplary unsubstituted alkoxy groups include $C_{1-3}$, $C_{1-6}$, $C_{1-12}$, $C_{1-16}$, $C_{1-18}$, $C_{1-20}$, or $C_{1-24}$ alkoxy groups.

By "alkoxyalkyl" is meant an alkyl group, as defined herein, which is substituted with an alkoxy group, as defined herein. Exemplary unsubstituted alkoxyalkyl groups include between 2 to 12 carbons ($C_{2-12}$ alkoxyalkyl), as well as those having an alkyl group with 1 to 6 carbons and an alkoxy group with 1 to 6 carbons (i.e., $C_{1-6}$ alkoxy-$C_{1-6}$ alkyl).

By "alkoxycarbonyl" is meant an alkoxy group, as defined herein, that is attached to the parent molecular group through a carbonyl group. In some embodiments, an unsubstituted alkoxycarbonyl group is a $C_{2-7}$ alkoxycarbonyl group.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy; (2) $C_{1-6}$ alkylsulfinyl; (3) $C_{1-6}$ alkylsulfonyl; (4) amino; (5) aryl; (6) arylalkoxy; (7) aryloyl; (8) azido; (9) cyano; (10) carboxyaldehyde; (11) $C_{3-8}$ cycloalkyl; (12) halo; (13) heterocyclyl; (14) heterocyclyloxy; (15) heterocyclyloyl; (16) hydroxyl; (17) N-protected amino; (18) nitro; (19) oxo; (20) $C_{3-8}$ spirocyclyl; (21) $C_{1-6}$ thioalkoxy; (22) thiol; (23) —$CO_2R^A$, where $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —$C(O)NR^BR^C$, where each of $R^B$ and $R^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —$SO_2RD$, where RD is selected from the group consisting of (a) $C_{1-6}$ alkyl, (b) $C_{4-18}$ aryl, and (c) $C_{1-6}$ alk-$C_{4-18}$ aryl; (26) —$SO_2NR^ER^F$, where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —$NR^GR^H$, where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "alkyleneoxy" is meant an alkylene group, as defined herein, attached to the parent molecular group through an oxygen atom.

By "alkynyl" is meant an optionally substituted $C_{2-24}$ alkyl group having one or more triple bonds. The alkynyl group can be cyclic or acyclic and is exemplified by ethynyl, 1-propynyl, and the like. The alkynyl group can also be substituted or unsubstituted. For example, the alkynyl group can be substituted with one or more substitution groups, as described herein for alkyl.

By "amino" is meant —$NR^{N1}R^{N2}$, where each of $R^{N1}$ and $R^{N2}$ is, independently, H or optionally substituted alkyl, or $R^{N1}$ and $R^{N2}$, taken together with the nitrogen atom to which each are attached, form a heterocyclyl group, as defined herein.

By "aminoalkyl" is meant an alkyl group, as defined herein, substituted by an amino group, as defined herein.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl; (2) $C_{1-6}$ alkyl; (3) $C_{1-6}$ alkoxy; (4) $C_{1-6}$ alkoxy-$C_{1-6}$ alkyl; (5) $C_{1-6}$ alkylsulfinyl; (6) $C_{1-6}$ alkylsulfinyl-$C_{1-6}$ alkyl; (7) $C_{1-6}$ alkylsulfonyl; (8) $C_{1-6}$ alkylsulfonyl-$C_{1-6}$ alkyl; (9) aryl; (10) amino; (11) $C_{1-6}$ aminoalkyl; (12) heteroaryl; (13) $C_{1-6}$ alk-$C_4$ is aryl; (14) aryloyl; (15) azido; (16) cyano; (17) $C_{1-6}$ azidoalkyl; (18) carboxyaldehyde; (19) carboxyaldehyde-$C_{1-6}$ alkyl; (20) $C_{3-8}$ cycloalkyl; (21) $C_{1-6}$ alk-$C_{3-8}$ cycloalkyl; (22) halo; (23) $C_{1-6}$ haloalkyl; (24) heterocyclyl; (25) heterocyclyloxy; (26) heterocyclyloyl; (27) hydroxyl; (28) $C_{1-6}$ hydroxyalkyl; (29) nitro; (30) $C_{1-6}$ nitroalkyl; (31) N-protected amino; (32) N-protected amino-$C_{1-6}$ alkyl; (33) oxo; (34) $C_{1-6}$ thioalkoxy; (35) thio-$C_{1-6}$ alkoxy-$C_{1-6}$ alkyl; (36) —$(CH_2)_rCO_2R^A$, where r is an integer of from zero to four, and $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —$(CH_2)_rCONR^BR^C$, where r is an integer of from zero to four and where each $R^B$ and $R^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —$(CH_2)_rSO_2RD$, where r is an integer of from zero to four and where RD is selected from the group consisting of (a) $C_{1-6}$ alkyl, (b) $C_{4-18}$ aryl, and (c) $C_{1-6}$ alk-$C_{4-18}$ aryl; (39) —$(CH_2)_rSO_2NR^ER^F$, where r is an integer of from zero to four and where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —$(CH_2)_r$ NRGRH, where r is an integer of from zero to four and where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl; (43) perfluoroalkoxy; (44) aryloxy; (45) cycloalkoxy; (46) cycloalkylalkoxy; and (47) arylalkoxy. In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "arylene" is meant a multivalent (e.g., bivalent, trivalent, tetravalent, etc.) form of an aryl group, as described herein. Exemplary arylene groups include phenylene, naphthylene, biphenylene, triphenylene, diphenyl ether, acenaphthenylene, anthrylene, or phenanthrylene. In some embodiments, the arylene group is a $C_{4-18}$, $C_{4-14}$, $C_{4-12}$, $C_{4-10}$, $C_{6-18}$, $C_{6-14}$, $C_{6-12}$, or $C_{6-10}$ arylene group.

The arylene group can be branched or unbranched. The arylene group can also be substituted or unsubstituted. For example, the arylene group can be substituted with one or more substitution groups, as described herein for aryl.

By "aryleneoxy" is meant an arylene group, as defined herein, attached to the parent molecular group through an oxygen atom.

By "arylalkoxy" is meant an alkaryl group, as defined herein, attached to the parent molecular group through an oxygen atom.

By "aryloxy" is meant —OR, where R is an optionally substituted aryl group, as described herein. In some embodiments, an unsubstituted aryloxy group is a $C_{4-18}$ or $C_{6-18}$ aryloxy group.

By "aryloxycarbonyl" is meant an aryloxy group, as defined herein, that is attached to the parent molecular group through a carbonyl group. In some embodiments, an unsubstituted aryloxycarbonyl group is a $C_{5-19}$ aryloxycarbonyl group.

By "aryloyl" is meant an aryl group that is attached to the parent molecular group through a carbonyl group. In some embodiments, an unsubstituted aryloyl group is a $C_{7-11}$ aryloyl group.

By "azido" is meant an —$N_3$ group.

By "azo" is meant an —N=N— group.

By "azidoalkyl" is meant an azido group attached to the parent molecular group through an alkyl group, as defined herein.

By "carbonyl" is meant a —C(O)— group, which can also be represented as >C=O.

By "carboxyaldehyde" is meant a —C(O)H group.

By "carboxyaldehydealkyl" is meant a carboxyaldehyde group, as defined herein, attached to the parent molecular group through an alkylene group, as defined herein.

By "carboxyl" is meant a —$CO_2H$ group.

By "cyano" is meant a —CN group.

By "cycloalkyl" is meant a monovalent saturated or unsaturated non-aromatic cyclic hydrocarbon group of from three to twenty-four carbons, unless otherwise specified, and is exemplified by cyclopropyl, cyclobutyl, cyclopentyl, cyclohexyl, cycloheptyl, bicyclo[2.2.1.]heptyl and the like. The cycloalkyl group can also be substituted or unsubstituted. For example, the cycloalkyl group can be substituted with one or more groups including those described herein for alkyl. In some embodiments, the cycloalkyl group is a $C_{3-6}$, $C_{3-8}$, $C_{3-12}$, $C_{3-16}$, $C_{3-18}$, $C_{3-20}$, or $C_{3-24}$ cycloalkyl group.

By "cycloalkylene" is meant a multivalent (e.g., bivalent, trivalent, tetravalent, etc.) form of a cycloalkyl group, as described herein. Exemplary cycloalkylene groups include cyclopropylene, cyclobutylene, etc. In some embodiments, the cycloalkylene group is a $C_{3-6}$, $C_{3-8}$, $C_{3-12}$, $C_{3-16}$, $C_{3-18}$, $C_{3-20}$, or $C_{3-24}$ cycloalkylene group. The cycloalkylene group can be branched or unbranched. The cycloalkylene group can also be substituted or unsubstituted. For example, the cycloalkylene group can be substituted with one or more substitution groups, as described herein for alkyl.

By "cycloalkoxy" is meant a cycloalkyl group, as defined herein, attached to the parent molecular group through an oxygen atom.

By "halo" is meant F, $C_1$, Br, or I.

By "haloalkyl" is meant an alkyl group, as defined herein, substituted with one or more halo.

By "heteroalkyl" is meant an alkyl group, as defined herein, containing one, two, three, or four non-carbon heteroatoms (e.g., independently selected from the group consisting of nitrogen, oxygen, phosphorous, sulfur, or halo).

By "heteroalkylene" is meant a divalent form of an alkylene group, as defined herein, containing one, two, three, or four non-carbon heteroatoms (e.g., independently selected from the group consisting of nitrogen, oxygen, phosphorous, sulfur, or halo).

By "heteroalkyleneoxy" is meant a heteroalkylene group, as defined herein, attached to the parent molecular group through an oxygen atom.

By "heteroaryl" is meant a subset of heterocyclyl groups, as defined herein, which are aromatic, i.e., they contain 4n+2 pi electrons within the mono- or multicyclic ring system.

By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, benzodioxolyl, furyl, furanyl, thienyl, thiazolidinyl, isothiazolyl, isoindazolyl, triazolyl, tetrazolyl, oxotetrazolyl, tetrazolinyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, quinuclidinyl, and the like. The heterocyclyl group can be substituted with one, two, three, four, or five substituents independently selected from the group consisting of: (1) $C_{1-6}$ alkanoyl; (2) $C_{1-6}$ alkyl; (3) $C_{1-6}$ alkoxy; (4) $C_{1-6}$ alkoxy-$C_{1-6}$ alkyl; (5) $C_{1-6}$ alkylsulfinyl; (6) $C_{1-6}$ alkylsulfinyl-$C_{1-6}$ alkyl; (7) $C_{1-6}$ alkylsulfonyl; (8) $C_{1-6}$ alkylsulfonyl-$C_{1-6}$ alkyl; (9) aryl; (10) amino; (11) $C_{1-6}$ aminoalkyl; (12) heteroaryl; (13) $C_{1-6}$ alk-$C_{4-18}$ aryl; (14) aryloyl; (15) azido; (16) cyano; (17) $C_{1-6}$ azidoalkyl; (18) carboxyaldehyde; (19) carboxyaldehyde-$C_{1-6}$ alkyl; (20) $C_{3-8}$ cycloalkyl; (21) $C_{1-6}$ alk-$C_{3-8}$ cycloalkyl; (22) halo; (23) $C_{1-6}$ haloalkyl; (24) heterocyclyl; (25) heterocyclyloxy; (26) heterocyclyloyl; (27) hydroxyl; (28) $C_{1-6}$ hydroxyalkyl; (29) nitro; (30) $C_{1-6}$ nitroalkyl; (31) N-protected amino; (32) N-protected amino-$C_{1-6}$ alkyl; (33) oxo; (34) $C_{1-6}$ thioalkoxy; (35) thio-$C_{1-6}$ alkoxy-$C_{1-6}$ alkyl; (36) —$(CH_2)_rCO_2R^A$, where r is an integer of from zero to four, and $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —$(CH_2)_rCONR^BR^C$, where r is an integer of from zero to four and where each $R^B$ and $R^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —$(CH_2)_rSO_2RD$, where r is an integer of from zero to four and where RD is selected from the group consisting of (a) $C_{1-6}$ alkyl, (b) $C_{4-18}$ aryl, and (c) $C_{1-6}$ alk-$C_{4-18}$ aryl; (39) —$(CH_2)_rSO_2NR^ER^F$, where r is an integer of from zero to four and where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —$(CH_2)_rNR^GR^H$, where r is an integer of from zero to four and where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl; (43) perfluoroalkoxy; (44) aryloxy; (45) cycloalkoxy; (46) cycloalkylalkoxy; and (47) arylalkoxy.

By "heterocyclyloxy" is meant a heterocyclyl group, as defined herein, attached to the parent molecular group through an oxygen atom.

By "heterocyclyloxycarbonyl" is meant an heterocyclyloxy group, as defined herein, that is attached to the parent molecular group through a carbonyl group. In some embodiments, an unsubstituted heterocyclyloxycarbonyl group is a $C_{2-12}$ heterocyclyloxycarbonyl group.

By "heterocyclyloyl" is meant a heterocyclyl group, as defined herein, attached to the parent molecular group through a carbonyl group.

By "hydroxyl" is meant —OH.

By "hydroxyalkyl" is meant an alkyl group, as defined herein, substituted by one to three hydroxyl groups, with the proviso that no more than one hydroxyl group may be attached to a single carbon atom of the alkyl group and is exemplified by hydroxymethyl, dihydroxypropyl, and the like.

By "imino" is meant —NH—.

By "nitrilo" is meant —N<. Exemplary nitrilo groups include —$NR^{L3}$—, where $R^{L3}$ is H, optionally substituted alkyl, optionally substituted haloalkyl, optionally substituted alkoxy, optionally substituted alkaryl, optionally substituted aryl, or halo.

By "nitro" is meant an —$NO_2$ group.

By "nitroalkyl" is meant an alkyl group, as defined herein, substituted by one to three nitro groups.

By "nitroso" is meant an —NO group.

By "oxo" is meant an =O group.

By "oxy" is meant —O—.

By "perfluoroalkyl" is meant an alkyl group, as defined herein, having each hydrogen atom substituted with a fluorine atom. Exemplary perfluoroalkyl groups include trifluoromethyl, pentafluoroethyl, etc.

By "protecting group" is meant any group intended to protect a reactive group against undesirable synthetic reactions. Commonly used protecting groups are disclosed in "Greene's Protective Groups in Organic Synthesis," John Wiley & Sons, New York, 2007 (4th ed., eds. P. G. M. Wuts and T. W. Greene), which is incorporated herein by reference. O-protecting groups include an optionally substituted alkyl group (e.g., forming an ether with reactive group O), such as methyl, methoxymethyl, methylthiomethyl, benzoyloxymethyl, t-butoxymethyl, etc.; an optionally substituted alkanoyl group (e.g., forming an ester with the reactive group O), such as formyl, acetyl, chloroacetyl, fluoroacetyl (e.g., perfluoroacetyl), methoxyacetyl, pivaloyl, t-butylacetyl, phenoxyacetyl, etc.; an optionally substituted aryloyl group (e.g., forming an ester with the reactive group O), such as —C(O)—Ar, including benzoyl; an optionally substituted alkylsulfonyl group (e.g., forming an alkylsulfonate with reactive group O), such as —$SO_2$—$R^{S1}$, where $R^{S1}$ is optionally substituted $C_{1-12}$ alkyl, such as mesyl or benzylsulfonyl; an optionally substituted arylsulfonyl group (e.g., forming an arylsulfonate with reactive group O), such as —$SO_2$—$R^{S4}$, where $R^{S4}$ is optionally substituted $C_{4-18}$ aryl, such as tosyl or phenylsulfonyl; an optionally substituted alkoxycarbonyl or aryloxycarbonyl group (e.g., forming a carbonate with reactive group O), such as —C(O)—$ORT$" where $R^{T1}$ is optionally substituted $C_{1-12}$ alkyl or optionally substituted $C_{4-18}$ aryl, such as methoxycarbonyl, methoxymethylcarbonyl, t-butyloxycarbonyl (Boc), or benzyloxycarbonyl (Cbz); or an optionally substituted silyl group (e.g., forming a silyl ether with reactive group O), such as —Si—$(R^{T2})_3$, where each $R^{T2}$ is, independently, optionally substituted $C_{1-12}$ alkyl or optionally substituted $C_{4-18}$ aryl, such as trimethylsilyl, t-butyldimethylsilyl, or t-butyldiphenylsilyl. N-protecting groups include, e.g., formyl, acetyl, benzoyl, pivaloyl, t-butylacetyl, alanyl, phenylsulfonyl, benzyl, Boc, and Cbz. Such protecting groups can employ any useful agent to cleave the protecting group, thereby restoring the reactivity of the unprotected reactive group.

By "salt" is meant an ionic form of a compound or structure (e.g., any formulas, compounds, or compositions described herein), which includes a cation or anion compound to form an electrically neutral compound or structure. Salts (e.g., simple salts having binary compounds, double salts, triple salts, etc.) are well known in the art. For example, salts are described in Berge S M et al., "Pharmaceutical salts," J. Pharm. Sci. 1977 Jan.;66(1):1-19; International Union of Pure and Applied Chemistry, "Nomenclature of Inorganic Chemistry," Butterworth & Co. (Publishers) Ltd., London, England, 1971 (2nd ed.); and in "Handbook of Pharmaceutical Salts: Properties, Selection, and Use," Wiley-VCH, Apr. 2011 (2nd rev. ed., eds. P. H. Stahl and C. G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

By "solvate" is meant a stabilized form of a compound or structure (e.g., any formulas, compounds, or compositions described herein, including anionic or cationic forms thereof) with one or more solvent molecules. Such forms can be stabilized by any useful interaction, such as electrostatic forces, van der Waals forces, or hydrogen bond formation. Exemplary solvates include hydrates (including one or more water molecules).

By "isomer" is meant a form of a compound or structure (e.g., any formulas, compounds, or compositions described herein) having the same molecular formula but different line formula and/or different stereochemical formula. Exemplary isomers include structural isomers or stereoisomers (e.g., diastereomers or enantiomers).

By "anhydrate" is meant a form of a compound or structure (e.g., any formulas, compounds, or compositions described herein) generally lacking solvent molecules.

By "spirocyclyl" is meant an alkylene diradical, both ends of which are bonded to the same carbon atom of the parent group to form a spirocyclyl group and also a heteroalkylene diradical, both ends of which are bonded to the same atom. An unsubstituted spirocyclyl group can include an alkylene group, as defined herein, optionally containing one, two, three, or four non-carbon heteroatoms (e.g., independently selected from the group consisting of nitrogen, oxygen, phosphorous, sulfur, or halo). In some embodiments, the spirocyclyl group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ spirocyclyl group.

By "sulfinyl" is meant an —S(O)— group.
By "sulfo" is meant an —S(O)$_{20}$H group.
By "sulfonyl" is meant an —S(O)$_2$— group.
By "thio" is meant an —S— group.
By "thiol" is meant an —SH group.
By "triflate" is meant an —OSO$_2$—CF$_3$ or —OTf group.

By "triflimide" is meant an —N(SO$_2$—CF$_3$)$_2$ or —NTf$_2$ group.
By "trifyl" or "Tf" is meant an —SO$_2$—CF$_3$ group.
By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

Other features and advantages of the invention will be apparent from the following description and the claims.

DETAILED DESCRIPTION OF THE INVENTION

Figure 1:
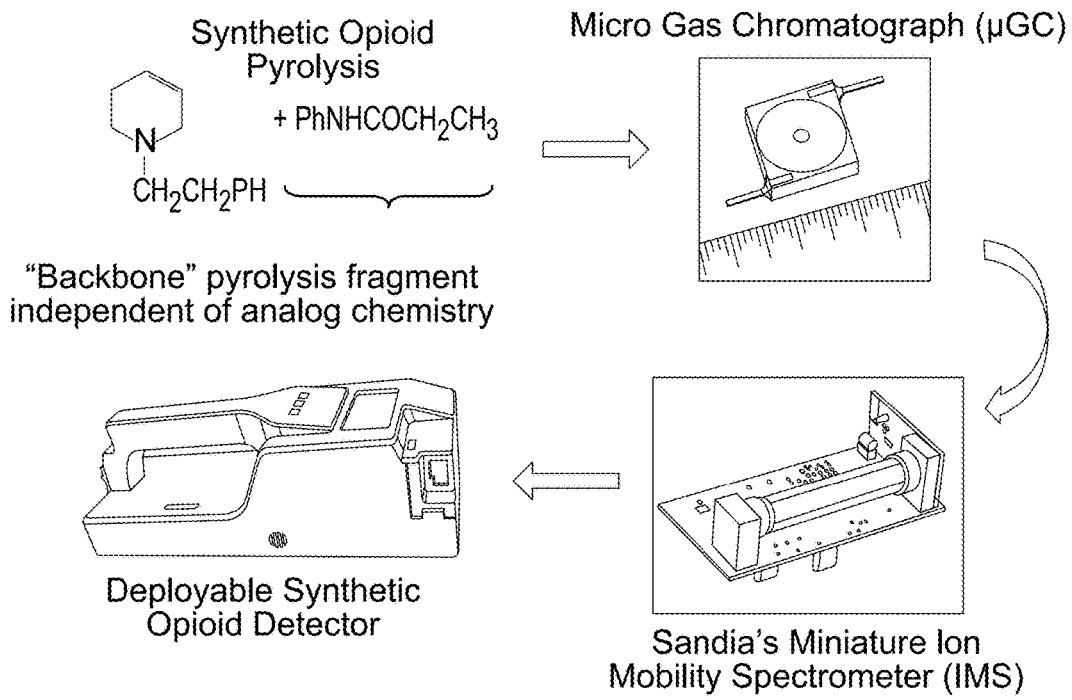
FIG. 1 shows an exemplary detection system that provides for pyrolysis of a suspected opioid sample, separation by way of micro gas chromatography, identification by use of a miniature mobility spectrometer (IMS), and possible integration of such components into a deployable synthetic opioid detector system.

The present invention relates to detection systems and methods that employ pyrolysis to obtain a backbone fragment of an opioid compound (e.g., any described herein). In particular embodiments, the systems and methods employ one or more components having micron-sized features, e.g., microchambers, microcolumns, microchannels, etc. In yet other embodiments, two or more components are provided as an integrated system, that is further amenable for portable deployment. FIG. 1 provides an exemplary system.

Figure 2A:
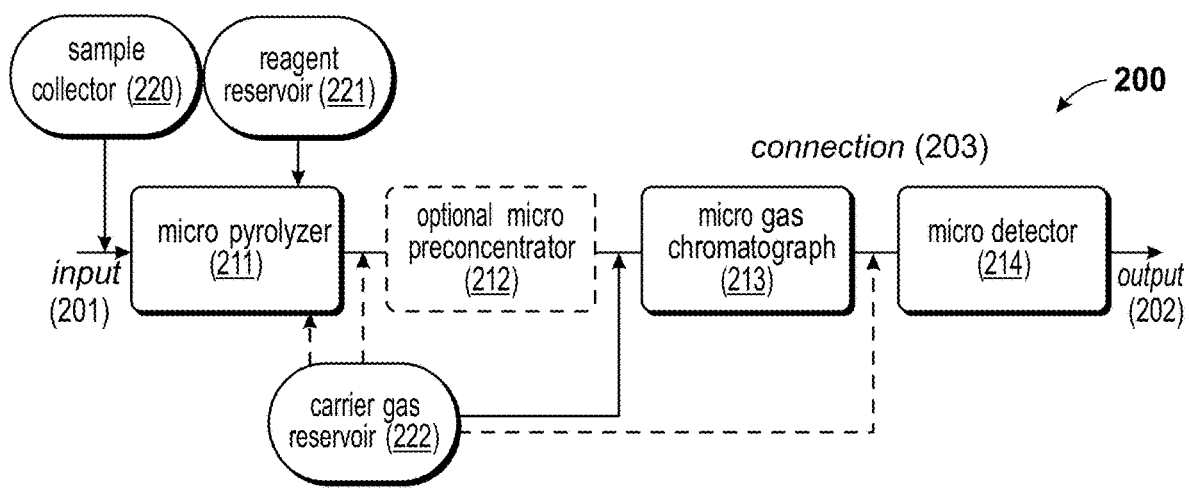
FIGS. 2A-2D provide schematics and structures of exemplary detection systems. Provided are (A) a schematic of an exemplary detection system 200 including a micro pyrolyzer 211, an optional micro preconcentrator 212, a micro gas chromatograph 213, and a micro detector 214; (B) photographs of exemplary structures for components of a detector system; and (C, D) exemplary microfabricated thermal structures for use as a micro pyrolyzer.

The detection systems can include any useful number and type of components to pyrolyze an opioid compound and detect an analyte (e.g., an opioid compound, a pyrolyzed opioid compound, a backbone fragment, and/or a secondary fragment). Exemplary, non-limiting components include a micro pyrolyzer, a micro preconcentrator, a micro gas chromatograph, a micro detection, a sample collector, a reagent reservoir, a carrier gas reservoir, as well as one or more carrier gas inlets and/or outlets. As seen in FIG. 2A, an exemplary system 200 includes an input 201 configured to provide a sample (e.g., an opioid compound) into the system (e.g., from a sample collector 220) and an output 202 configured to release the analyzed sample. The system 200 can also include a micro pyrolyzer 211 in fluidic communication with an input 201, in which a reagent reservoir 221 can be configured to deliver one or more reagents to the micro pyrolyzer 211 before, during, or after pyrolysis. In particular embodiments, the micro pyrolyzer 211 includes an inlet in fluidic communication with the sample collector 220.

An optional micro preconcentrator 212 can be provided to be in fluidic communication with an outlet of the micro pyrolyzer 211. Such a preconcentrator can be configured to releasably sorb the backbone fragment, thereby increasing the local spatial or temporal concentration of the fragment to be detected.

A micro gas chromatograph 213 can be in fluidic communication with an outlet of the micro pyrolyzer 211 or to be in fluidic communication with an outlet of the optional micro preconcentrator 212. The micro gas chromatograph (micro GC) can include one or more columns configured to interact with the backbone fragment, e.g., by way of a stationary phase disposed on a surface of the column, in which the stationary phase interacts with the backbone fragment.

A micro detector 214 can be in fluidic communication with an outlet of the micro gas chromatograph 213. The micro detector can include any useful sensor configured to detect the presence of the backbone fragment. If desired, one or more secondary fragments from pyrolysis can also be preconcentrated (e.g., by use of a micro preconcentrator), separated (e.g., by use of a micro gas chromatograph), and/or detected (e.g., by use of a micro detector). Accordingly, any component, inlet, outlet, or connection described herein to contain or transport the backbone fragment can be further configured for use with one or more secondary fragments.

The system can include a carrier gas reservoir 222, in which a carrier gas is employed to transport a backbone fragment or a secondary fragment from one component to another component (e.g., the micro pyrolyzer to the micro GC, the micro pyrolyzer to the micro preconcentrator, the micro preconcentrator to the micro GC, the micro GC to the micro detector, etc.). Thus, any useful number of connections 203 can be present between different components.

Figure 2B:
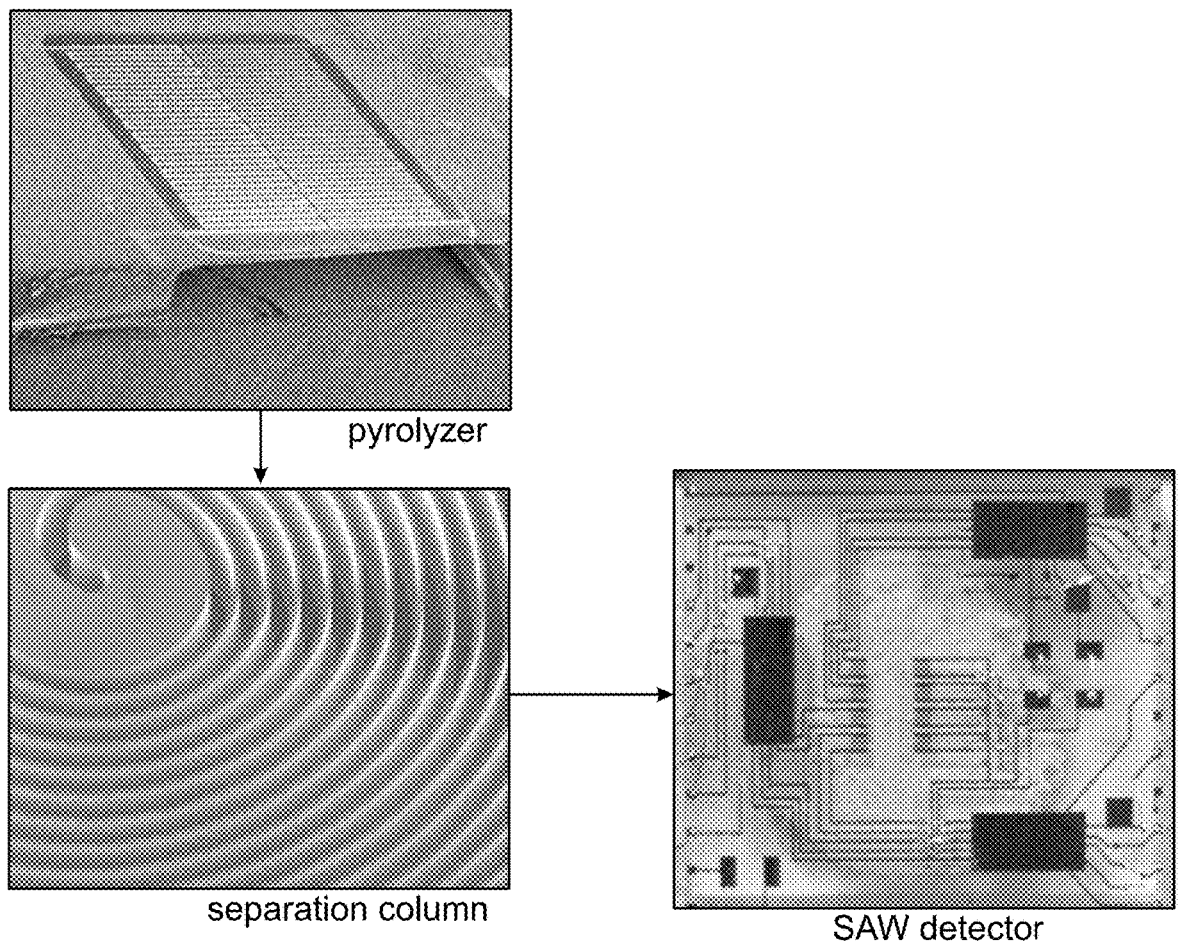
Figure 2C:
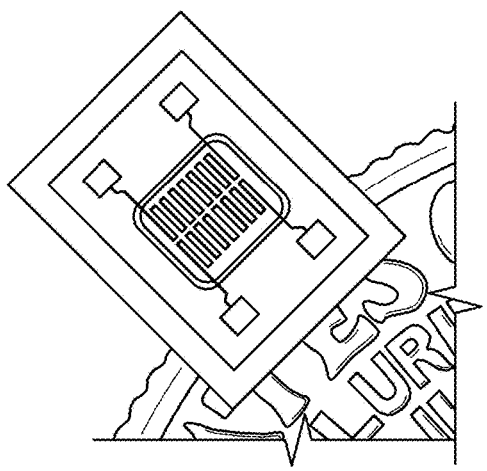
Figure 2D:
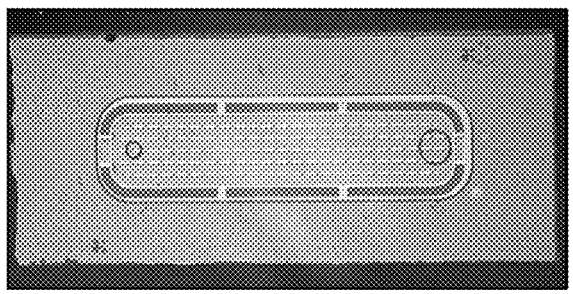

FIG. 2B provides exemplary components, including a pyrolyzer, a separation column, and a surface acoustic wave (SAW) detector. The pyrolyzer can have any useful configuration, such as microfabricated thermal structures shown in FIGS. 2C-2D. Additional components are described herein. Yet other additional components (e.g., one or more micro pyrolyzers, micro gas chromatographs, micro detectors, and/or micro preconcentrators) are described in Adkins D et al., "Advanced detectors for chemical weapon detection," presented at the Second Joint Conference on Point Detection for Chemical and Biological Defense, held on 1-5 Mar. 2004 in Williamsburg, Va. (7 pp.); Arana L R et al., "A micro-fabricated suspended-tube chemical reactor for fuel processing," Technical Digest. MEMS 2002 IEEE International Conference. Fifteenth IEEE International Conference on Micro Electro Mechanical Systems, held on 24 Jan. 2002 in Las Vegas, Nev., pp. 232-5; Brocato T A et al., "Investigations into the chemical structure based selectivity of the microfabricated nitrogen-phosphorus detector," Sens. Actuat. B 2016; 224:618-23; Casalnuovo S A et al., "Gas phase chemical detection with an integrated chemical analysis system," Proceedings of the 1999 Joint Meeting of the European Frequency and Time Forum and the IEEE International Frequency Control Symposium, held on 13-16 Apr. 1999 in Besancon, France (6 pp.); Cavicchi R E et al., "Micro-hotplate gas sensor," Solid-State Sensor and Actuators Workshop, held on 13-16 Jun. 1994 in Hilton Head, S. C., pp. 53-6; Cruz D et al., "Microfabricated thermal conductivity detector for the micro-ChemLab™," Sens. Actuat. B 2007; 121:414-22; Frye-Mason G et al., "Hand-held miniature chemical analysis system (ChemLab) for detection of trace concentrations of gas phase analytes," in van den Berg A, Olthuis W & Bergveld P (eds), Micro TotalAnalysis Systems 2000 (Springer, Dordrecht), 2000, pp. 229-32; Frye-Mason G et al., "Expanding the capabilities and applications of gas phase miniature chemical analysis systems (pChemLab™)," in Ramsey J M & van den Berg A (eds), Micro TotalAnalysis Systems 2001 (Springer, Dordrecht), 2001, pp. 658-60; Frye-Mason G C et al., "Microfabricated gas phase chemical analysis system," Digest of Papers for Microprocesses and Nanotechnology '99, held on 6-8 Jul. 1999 in Yokohama, Japan, pp. 60-1; Frye-Mason G C et al., "Integrated chemical analysis systems for gas phase CW agent detection," in Harrison D J & van den Berg A (eds), Micro Total Analysis Systems '98 (Springer, Dordrecht), 1998, pp 477-81; Gall M, "The Si-Planar-Pellistor array, a detection unit for combustible gases," Sens. Actuat. B 1993; 15-16:260-4; Grate J W, "Acoustic wave microsensor arrays for vapor sensing," Chem. Rev. 2000; 100:2627-48; Havey C D et al., "Evaluation of a micro-fabricated pyrolyzer for the detection of *Bacillus anthracis* spores," J. Anal. Appl. Pyrolysis 2004; 72:55-61; Hudson M L et al., "Design, testing, and simulation of microscale gas chromatography columns," International Mechanical Engineering Congress and Exposition, held on 15-20 Nov. 1998 in Anaheim, Calif. (8 pp.); Johnson R S et al., "Thermally-activated pentanol delivery from precursor poly(p-phenylenevinylene)s for MEMS lubrication," Macromolec. Rapid Commun. 2012; 33:1346-50; Kottenstette R et al., "Development and testing of Sandia's CWA point detector technology," presented at the Second Joint Conference on Point Detection for Chemical and Biological Defense, held on 1-5 Mar. 2004 in Williamsburg, Va. (7 pp.); Lewis P R et al., "Recent advancements in the gas-phase MicroChemLab," IEEE Sensors J. 2006; 6:784-95; Manginell R P et al., "Microfabrication of membrane-based devices by deep-reactive ion etching (DRIE) of silicon," Proceeding of the Symposium on Microstructures and Microfabricated Systems IV, presented at the 194$^{th}$ Meeting of the Electrochemical Society, held on 1-6 Nov. 1998 in Boston, Mass., pp. 62-9; Manginell R P et al., "Finite element modeling of a microhotplate for microfluidic applications," Modeling and Simulation of Microsystems (MSM '99) conference, held on 19-21 Apr. 1999 in San Juan, Puerto Rico (4 pp.); Manginell R P et al., "Microfabricated planar preconcentrator," Solid-State Sensors and Actuators Workshop, held on 4-8 Jun. 2000 in Hilton Head, S.C. (3 pp.); Manginell R P et al., "Two-dimensional modeling and simulation of mass transport in microfabricated preconcentrators," IEEE Sensors J.

2007; 7:1032-41; Manginell R P et al., "Monolithically-integrated MicroChemLab™ for gas-phase chemical analysis," 7th International Conference on Miniaturized Chemical and Biochemical Analysis Systems, held on 5-9 Oct. 2003 in Squaw Valley, Calif., pp. 1247-50; Manginell R P et al., "A monolithically-integrated GC chemical sensor system," Sensors 2011; 11:6517-32; Manginell R P et al., "Mass-sensitive microfabricated chemical preconcentrator," J. Microelectromech. Sys. 2008; 17:1396-407; Manginell R P et al., "In-situ monitoring of micro-chemical vapor deposition (µ-CVD): experimental results and SPICE modeling," 1998 Solid-State Sensors and Actuators Workshop, held on 7-11 Jun. 1998 in Hilton Head Island, S.C. (4 pp.); Manginell R P et al., "Selective, pulsed CVD of platinum on microfilament gas sensors," 1996 Solid-State Sensor and Actuator Workshop, held on 2-6 Jun. 1996 in Hilton Head Island, S.C. (4 pp.); Manginell R P et al., "Microfabrication of membrane-based devices by HARSE and combined HARSE/wet etching," Proc. SPIE 1998; 3511:269-76; Manginell R P et al., "Overview of micromachined platforms for thermal sensing and gas detection," Proc. SPIE 1997; 3046:273-84; Martin S J et al., "Gas sensing with acoustic devices," IEEE Ultrasonics Symposium 1996:423-34; Martin S J et al., "Magnetically-excited flexural plate wave resonator," IEEE Trans. Ultrasonics Ferroelectr. Freq. Control 1998; 45:1381-7; Matzke C M et al., "Microfabricated silicon gas chromatographic microchannels: fabrication and performance," Proc. SPIE 1998; 3511:262-8; Moorman M et al., "Microcombustor array and micro-flame ionization detector for hydrocarbon detection," Proc. SPIE 2003; 4981:40-50; Morgan C H et al., "Rapid identification of bacteria with miniaturized pyrolysis/GC analysis," Proc. SPIE 2001; 4205:199-206; Park J et al., "Vapor recognition with small arrays of polymer-coated microsensors: a comprehensive analysis," Anal. Chem. 1999; 71:3877-86; Pfeifer K B et al., "Measurement of ion swarm distribution functions in miniature low-temperature co-fired ceramic ion mobility spectrometer drift tubes," Anal. Chem. 2005; 77:5215-20; Pfeifer K B et al., "Signal-to-noise and resolution enhancement in ion mobility spectrometry using correlation gating techniques: Barker codes," IEEE Sensors J. 2007; 7:1130-7; Schwindt P D D et al., "A highly miniaturized vacuum package for a trapped ion atomic clock," Rev. Sci. Instruments 2016; 87:053112 (9 pp.); Simonson R J et al., "Microfabricated nitrogen-phosphorous detector: chemically mediated thermionic emission," Sandia Report SAND2012-7778, 2012 (51 pp.); Srinivasan R et al., "Micromachined chemical reactors for surface catalyzed oxidation reactions," 1996 Solid-State Sensor and Actuator Workshop, held on 2-6 Jun. 1996 in Hilton Head Island, S.C. (4 pp.); Terry S.C. et al., "A gas chromatography air analyzer fabricated on a silicon wafer," IEEE Trans. Electron Devices 1979;ED-26:1880-6; Tian W C et al., "Microfabricated preconcentrator-focuser for a microscale gas chromatograph," J. Microelectromech. Sys. 2003; 12:264-72; Wang D et al., "Sol-gel column technology for single-step deactivation, coating, and stationary-phase immobilization in high-resolution capillary gas chromatography," Anal. Chem. 1997; 69:4566-76; Whiting J J et al., "ChemLab: twenty years of developing CBRNE detection systems with low false alarm rates," Proc. SPIE 2019; 11010:1101012 (13 pp.); Whiting J J et al.," High-speed two-dimensional gas chromatography using microfabricated GC columns combined with nanoelectromechanical mass sensors," presented at Transducers 2009, held on 21-25 Jun. 2009 in Denver, Colo. (pp. 1666-9); Whiting J J et al., "A high-speed, high-performance, microfabricated comprehensive two-dimensional gas chromatograph," Lab Chip 2019; 19:1633-43; Wunsch T F et al., "Recent advances in AC-DC transfer measurements using thin-film thermal converters," Proc. Measurement Science Conference, held on 18-19 Jan. 2001 in Anaheim, Calif.; Zanini M et al., "Fabrication and properties of a Si-based high sensitivity microcalorimetric gas sensor," Solid-State Sensor and Actuator Workshop, held on 13-16 Jun. 1994 in Hilton Head, S.C., p. 176-9; Zimmermann S et al., "Micro flame ionization detector and micro flame spectrometer," Sens. Actuat. B 2000; 63:159-66; and Zimmermann S et al., "Miniaturized flame ionization detector for gas chromatography," Sens. Actuat. B 2002; 83:285-9, each of which is incorporated herein by reference in its entirety.

Yet other additional components (e.g., one or more micro pyrolyzers, micro gas chromatographs, micro detectors, and/or micro preconcentrators) are described in U.S. Pat. Nos. 3,954,819; 3,992,174; 4,408,125; 4,710,354; 4,837, 374; 4,980,131; 5,367,164; 5,472,670; 5,550,062; 5,820, 922; 5,825,025; 5,834,627; 6,068,684; 6,171,378; 6,527, 835; 6,627,881; 6,666,907; 6,669,392; 6,786,716; 6,939, 632; 6,972,406; 7,078,237; 7,168,298; 7,208,729; 7,422, 724; 7,727,314; 8,298,488; 10,197,532; and 10,261,048; and U.S. Pat. Pub. No. 2003/0224531, each of which is incorporated herein by reference in its entirety.

The system can optionally include one or more pumps, valves, lines, channels, exhausts, flow controls, inlets, outlets, films, interconnections, interconnectors, flow channels, etc., associated with a component or between a plurality of components. Systems can include one or more devices helpful for packaging, such as electronics, pins, fluidic components, magnets, thermal isolation units, etc. Furthermore, the system can include two or more components arranged in parallel analysis channels. Optionally, each analysis channel can include a serial connection of a plurality of components.

Micro Pyrolyzers

One or more micro pyrolyzers can be included within the system to pyrolyze a compound, thereby producing an analyte to be detected. In some non-limiting instances, the micro pyrolyzer can include a miniature hotplate including a heating element (e.g., a metal or an intermetallic compound, such as platinum, palladium, gold, tungsten, alumina, chromium, nickel, titanium, tantalum, silicon carbide, silicon, molybdenum, and/or molybdenum disilicide, as well as combinations thereof and alloys thereof, including patterns or wires thereof) disposed upon or in proximity to a substrate (e.g., a suspended membrane or an insulated platform of any useful material, such as silicon, polycrystalline silicon, silicon oxide, silicon oxynitride, silicon carbide, and/or silicon nitride). Such heating elements can include a material that has been optionally annealed. In other non-limiting instances, the micro pyrolyzer can include a resistive heating element disposed on a surface of a substrate. The heating element can include, e.g., a wire, a meandering resistor, a circuitous metal trace, etc.

In some embodiments, the micro pyrolyzer can include a resistive heating element and a substrate, in which both are formed from a heavily doped silicon (e.g., about 10 m thick, P-type device layer with a resistivity of 0.005-0.020 ohm-cm). In other embodiments, the micro pyrolyzer is a micro burner unit having a miniature nozzle configured to produce a stably burning flame (e.g., an oxyhydrogen flame).

In some embodiments, the micro pyrolyzer is provided on a substrate that is a pivot-plate resonator, in which a heating element is then disposed on that resonator.

Optionally, the micro pyrolyzer can include a catalyst in proximity to the heating element. In one embodiment, the catalyst is spray coated upon a surface of the heating element and/or upon a surface of the substrate in proximity to the heating element. The catalyst can include any useful material, including platinum, alumina, titanium, tin, zirconium, strontium, tantalum, a semiconducting oxide, hexaaluminate, and/or a noble metal (e.g., platinum or palladium), as well as oxides thereof (e.g., titanium oxide), mixtures thereof, combinations thereof, layers thereof, and slurries thereof. In any embodiment herein, the catalyst includes a supported catalyst (e.g., which in turn includes a catalyst material (e.g., a noble metal) and a support material (e.g., a high-temperature-stable and high-surface-area material)).

The substrate can include a coating, e.g., a sol gel coating, a polymer, a film, or a microporous oxide configured to interact with the compound and/or the analyte; and/or an adhesion layer (e.g., disposed between a substrate and a heating element, such as an adhesion layer including zinc, titanium, tantalum, as well as oxides thereof). The coating can include any catalyst described herein. In some embodiments, the micro pyrolyzer includes a Pt—ZnO microhotplate having a Pt base and a ZnO adhesion layer. A micro pyrolyzer can have three-dimensional features (e.g., three-dimensional fins) suspended within a substrate or upon a membrane to promote air flow (and to facilitate transport of compounds, analytes, and/or fragments) through the features during pyrolysis.

In other embodiments, the micro pyrolyzer has two-dimensional features (e.g., planar surface heaters), in which air flows across the surface of the micro pyrolyzer during pyrolysis.

A micro pyrolyzer can include an electrical control circuit connected to the heating element. In one embodiment, the electrical control circuit (e.g., including a constant temperature control circuit, a constant voltage control circuit, and/or a constant current control circuit) is configured to power the heating element and/or monitor a change in one or more electrical characteristics of the heating element in response to heat liberated from pyrolysis of the opioid compound on the micro pyrolyzer.

In one non-limiting embodiment, the micro pyrolyzer includes a substrate having a suspended membrane formed thereon; and a resistive heating element disposed on a surface of the membrane for heating of the membrane. In further embodiments, a catalyst is disposed on a surface of the membrane. In some embodiments, the micro pyrolyzer includes a substrate having a suspended membrane formed thereon; a lid disposed on a side on the membrane, thereby providing a combustion chamber; at least one reactant gas inlet attached to the combustion chamber for introducing a gas (e.g., a carrier gas and/or a reactant gas thereinto, in which the gas is configured to transport the opioid compound, as well as pyrolyzed compounds thereof, such as backbone fragments and/or secondary fragments); an exhaust gas outlet attached to the combustion chamber for removal of pyrolyzed compounds (e.g., pyrolysis products, backbone fragments, and/or secondary fragments therefrom); a resistive heating element disposed on a surface of the membrane for heating the membrane; and an optional catalyst disposed on the surface of the membrane exposed to the combustion chamber to provide for ignition of the gas and/or stabilization of a resulting combustion flame. In some embodiments, the micro pyrolyzer further includes an ion collection electrode disposed in proximity to the heating element, in which the electrode collects charge generated by the gas reacting on the heating element when the micro pyrolyzer is heated by the heating element and a voltage bias is applied between the micro pyrolyzer and the electrode.

In some embodiments, the micro pyrolyzer is a suspended tube reactor including at least one fluid conducting tube; and at least one thermally conductive structure in thermal communication with a first thermally insulating portion of the fluid conducting tube and a second thermally insulating portion of the fluid conducting tube. In some embodiments, the suspended tube reactor further includes a heating element (e.g., a resistive heater trace) disposed on an exterior surface of the thermally conductive region structure and heats the region to a desired operating temperature (e.g., any elevated temperatures or temperature ranges described herein).

In other embodiments, the micro pyrolyzer is a microbridge including a substrate; a suspended membrane formed therein and having a cavity formed within the substrate and beneath the membrane; and a resistive heating element disposed on a surface of the membrane or within the membrane for heating of the membrane.

In some embodiments, the micro pyrolyzer includes a substrate having a suspended membrane formed thereon, the membrane having a surface for accepting the sample, wherein the substrate is selected from the group consisting of semiconductors and dielectrics; and a resistive heating element disposed on the membrane.

In some embodiments, the micro pyrolyzer includes a substrate having a suspended membrane formed thereon; a lid disposed on a side on the membrane to thereby provide a combustion chamber; at least one gas inlet attached to the pyrolysis chamber for introduction of one or more gases thereinto; an exhaust gas outlet attached to the pyrolysis chamber for removal of pyrolysis products therefrom; a heating element disposed on a surface of the membrane for heating of the membrane; and a catalyst disposed on the surface of the membrane exposed to the pyrolysis chamber to provide for ignition of the one or more gases and stabilization of the resulting pyrolysis flame.

In some embodiments, the micro pyrolyzer includes a substrate; a first filament disposed on a surface of the substrate; and a second filament disposed on a surface of the substrate, further comprising a catalyst deposited on a surface of the second filament. In some embodiments, the first and second filaments include a conductive polycrystalline silicon and an insulating layer surrounding the conductive polycrystalline silicon, wherein the insulating layer includes silicon nitride. In other embodiments, the first and second filaments are parallel to each other, and an air gap is present between the first and second filaments.

Additional exemplary micro pyrolyzers, as well as structural components thereof, are described in U.S. Pat. Nos. 5,820,922; 5,834,627; 6,786,716; 6,939,632; 7,078,237; and 8,298,488, each which is incorporated herein by reference in its entirety.

Micro Gas Chromatographs

One or more micro gas chromatographs (or components for such gas chromatographs) can be included within the system. Such micro gas chromatograph (GC) components can be employed, in some instances, to separate portions of a sample, separate chemical components of a sample, and/or separate analytes within the sample. In particular embodiments, the GC can be employed to detect the presence of one or more opioid compound, pyrolyzed fragments of an opioid compound, a backbone fragment, and/or a secondary fragment (e.g., any described herein).

Exemplary components include one or more μGC columns. A μGC column can include any useful configuration, e.g., a groove, a channel, etc., having any useful dimension, e.g., a width of from about 10 µm to about 200 µm, a depth of from about 75 µm to about 600 µm, and a length of from about 0.1 m to 1 m. The µGC column can be formed from any useful material (e.g., silicon, nickel, glass, aluminum, stainless steel, and/or a polymer); and/or include an optional stationary phase (e.g., a sol gel, polyethylene glycol (PEG), polyepichlorohydrin (PECH), polysiloxane (e.g., poly(dimethylsiloxane), poly(diphenylsiloxane), poly(phenylmethylsiloxane), as well as combinations thereof), polyisobutylene (PIB), fluoropolyol (FPOL), poly(diphenoxyphosphazine) (PDPP), bis-cyanoallyl polysiloxane (OV-275), Carbowax, SPB-5, and OV-1).

The µGC column can be an open column, a porous layer open tubular column, or a packed column having a plurality of beads or particles. The µGC column can have any useful layout, such as a serpentine design, a spiral design, a double spiral design, etc., as well as any useful format, e.g., GCxGC. Any useful reactant gas or carrier gas can be employed (e.g., air, helium). The column can optionally be heated (e.g., by a resistance heating element deposited in proximity to the column, such as an unetched side of the substrate supporting the etched, planar column).

In some embodiments, the micro gas chromatography includes a micro µGC column having an intake end and a detector end, in which the column is formed by a series of parallel passages connected at alternating ends in a substantially planar microstructure. In other embodiments, the micro gas chromatography includes a micro µGC column having an intake end and a detector end, in which the column is formed by a single passage having a spiral or double spiral design in a substantially planar microstructure.

In some embodiments, the micro gas chromatography includes a micro µGC column having a substrate; a continuous channel formed in a first surface to the substrate, in which the continuous channel includes an inlet end and an outlet end; a lid bonded to the first surface of the substrate to seal the continuous channel; and an optional heating element deposited on the first surface of the substrate or on a second surface of the substrate that opposed the first surface. Optionally, the micro gas chromatography can further include a control board for electrical control of the heating element and fluidic control of the continuous channel, in which the control board is electrically connected to the heating element to heat the continuous channel. Furthermore, the micro gas chromatography can include an inlet tube in fluidic communication with the control board and the inlet end of the continuous channel, as well as an outlet tube in fluidic communication with the control board and the outlet end of the continuous channel. In some embodiments, the inlet tube and the outlet tube are thermally isolate the control board from the substrate.

Additional exemplary micro GC components are described in U.S. Pat. Nos. 6,068,684; 6,666,907; and 6,786, 716, each which is incorporated herein by reference in its entirety.

Micro Detectors

One or more useful micro detectors can be present within the system. Non-limiting exemplary detectors include a micro-thermal conductivity detector (TCD), a thermistor, a thermionic ionization detector (TID), a molecular electronic array (MEA), a miniature ion mobility spectrometer (IMS), a pulsed discharge ionization detector (PDID), a pulsed discharge helium ionization detector (PDHID), a surface acoustic wave (SAW) sensor (e.g., including a piezoelectric substrate, at least a pair of interdigitated transducers disposed on a surface of the substrate, and optional delay lines), a comb drive, a flexural plate wave (FPW) resonator, a nanoelectromechanical system (NEMS) cantilever resonator, a pivot-plate resonator (PPR) microbalance (e.g., including a plate suspended between two arms, a plurality of magnets configured to provide a magnetic field parallel to a surface of the plate, and an electrode disposed on the surface of the plate configured to oscillate the plate around the two arms), a nitrogen phosphorous detector (NPD) (e.g., including a bead and a metal wire configured to heat and support the bead), a nanoparticle ligand bridge (NPLB) resistor (e.g., including a plurality of nanoparticles disposed between two electrodes (e.g., nanoelectrodes), in which the nanoparticles are optionally distributed in a matrix), a flame ionization detector (FID), a flame photometric detector (FPD) (e.g., including an optical detector configured to detect light emission from excited atoms produced in proximity to the micro pyrolyzer, in which the optical detector can be an optical fiber, a spectrometer, and/or a photodetector), a microfabricated calorimetric detector (MCD), a magnetically-actuated flexural plate wave sensor (magFPW), an atomic emission detector (AED), a photodiode (PD), a pulsed flame photometric detector (PFPD), an electron captive detector (ECD), a mass spectrometer (MS), a Fourier transform infrared (FTIR) spectrometer, etc. A micro detector can include one or more coatings configured to selectively capture an analyte.

In some embodiments, the micro detector is a miniature ion mobility spectrometer including a first set of electrodes arranged linearly in a first direction and separated by a first set of gaps; a second set of electrodes positioned directly opposing the first set of electrodes to match the first set of electrodes on a one-to-one basis, wherein the second set of electrodes are separated by a second set of gaps; a drift region between the first set of electrodes and the second set of electrodes, wherein charged particles enter at a first end of the drift region and traverse the drift region along the first direction; and a detector positioned at a second end of the drift region configured to receive charged particles exiting the drift region.

In some embodiments, the micro detector is an ion mobility spectrometer (IMS). In some embodiments, the IMS includes an ionizing region for ionizing a vapor (e.g., including the opioid compound, backbone fragments, and/or secondary fragments) to form ions; a drift tube having a drift region in which the ions drift under the influence of an electric field, established by a plurality of stacked electrodes, against a counter-flowing drift gas and are separated into at least one single ion swarm therein; a gate for pulsing the ions into the drift region; and an ion collector for detecting the at least one single ion swarm at the end of the drift region to provide an ion mobility spectrum, wherein at least two of the stacked electrodes adjacent to the ion collector have an electrode pitch that less than the width of an ion swarm and each of the adjacent electrodes is connected to a source of free charge, thereby providing a virtual aperture grid at the end of the drift region that shields the ion collector from the mirror current of the ion swarm. In particular embodiments, the source of free charge includes a low-pass electrical circuit that has a cut-off frequency below a minimum frequency component of the ion swarm. In other embodiments, the source of free charge includes a capacitor.

In some embodiments, the IMS includes a drift tube with a gas inlet at one end and a gas outlet at the opposed end; an ionizing chamber connected to the gas outlet, the ionizing chamber being provided with a sample gas inlet port; a plurality of gating grid electrodes located between the drift tube and the ionizing region; and an exhaust outlet provided for near the ionizing chamber and away from the gating electrodes.

In some embodiments, the micro detector is a mass spectrometer including: an electron source comprising a first substrate with a cathode, a gate and a locating profile on its surface, a second substrate with an anode and a locating profile on its surface and a spacer adapted to co-operate with the locating profiles to maintain the substrates at a set distance and orientation with respect to one another so that the cathode, gate and anode together form an electron source; and a mass filter comprising first and second substrates each with a mass filtering component and a locating profile on its surface.

In particular embodiments, the micro detector is a mass spectrometer formed from two multilayer wafers, each wafer having a first layer, a second layer, and an insulating layer provided therebetween; the mass spectrometer having a plurality of electrode rods and a plurality of planar electrodes, the electrodes being formed in the first layer and electrode rods being provided in the second layer, the second layer being dimensioned to receive the electrode rods, the rods being retained in contact with the second layer by the provision of at least one silicon spring formed in the second layer.

Additional exemplary micro detectors, as well as structural components thereof, are described in U.S. Pat. Nos. 5,825,025; 6,786,716; 6,972,406; 7,208,729; 8,298,488; 10,197,532; and 10,261,048, each of which is incorporated herein by reference in its entirety.

Micro Preconcentrators

One or more useful micro preconcentrators can be present within the system. Non-limiting exemplary preconcentrators can include any useful configuration, such as a thermally isolated membrane. A micro preconcentrator can include one or more coatings configured to selectively capture an analyte, such as a polymer coating, microporous coating, a sol gel coating, and/or a sol gel oxide coating.

In some embodiments, the micro preconcentrator includes a substrate; a heating element (e.g. a resistive heating element) disposed on a surface of the substrate; and a sorptive material disposed on at least a portion of the surface of the substrate, wherein the sorptive material is configured to concentrate at least one analyte (e.g., opioid compound, backbone fragment, and/or secondary fragment), in which the at least one analyte can be released from the sorptive material upon heating of the sorptive material by the heating element. In further embodiments, the substrate further includes a suspended membrane formed thereof, in which the heating element is disposed on a surface of the suspended membrane.

In some embodiments, the micro preconcentrator includes a heat spreading layer disposed in proximity to the substrate and/or the heating element. In other embodiments, a control circuit can be included, in which the control circuit is configured for heating the heating element to a set temperature and/or measuring the power required to maintain the heating element at the set temperature when a gas flows.

In some embodiments, the micro preconcentrator includes a pivot plate resonator, which in turn includes a frame; a paddle having a first surface and a second surface for collection of the analyte thereon, the paddle further having a first end and a second end, wherein the paddle is pivotably anchored to the frame by pivot arms at each end of the paddle and wherein the pivot arms define an axis of rotation of the paddle; a current conductor line disposed on a surface of the paddle that is displaced from the axis of rotation of the paddle; and a heating element disposed on a surface of the paddle, wherein the heating element is configured to thermally release the collected analyte from the paddle.

In particular embodiments, the micro preconcentrator further includes a magnetic field source (e.g., a permanent magnet, a semi-permanent magnet, a direct current coil, etc.) configured to apply a static magnetic field aligned substantially in-plane with the paddle and substantially perpendicular to the current conductor line and the axis of rotation. In other embodiments, the micro preconcentrator includes a power source configured to energize the current conductor line with an alternating electrical current to excite an oscillatory motion of the paddle about the axis of rotation.

In some embodiments, the micro preconcentrator further includes a chemically sensitive coating disposed on at least one surface of the paddle. In yet other embodiments, the micro preconcentrator includes an insulating thin film on a surface of the paddle to provide electrical isolation of the current conductor line.

In other embodiments, the micro preconcentrator includes a platform having a substrate, a suspended membrane formed thereon, and a heating element configured to heat the membrane; and at least one active polymer film disposed on a flow-channel-side of the membrane. In some embodiments, the active polymer films is configured to absorb at least one analyte from a sample in a flow channel of the platform when the active polymer film is heated above a critical transition temperature and desorbs the at least one analyte when the active polymer film is cooled below the critical transition temperature. In particular embodiments, the micro preconcentrator includes a thermoelectric converter configured to actively cool the active polymer film below the critical transition temperature. In some embodiments, the active polymer film includes a hydrogel (e.g., poly(ethylene oxide) or poly(n-isopropylacrylamide)).

In some embodiments, the micro preconcentrator includes a heating element disposed on a first portion of a substrate; a sorptive material to sorb and concentrate at least one analyte of interest from a vapor over time, said at least one analyte being releasable from said sorptive material upon heating of said sorptive material by said heating element, said sorptive material disposed on said heating element to create a sorbent zone; and a plurality of thermal isolation support structures fabricated from a second portion of said substrate that connects said first portion of said substrate to a third portion of said substrate, with each thermal isolation support structure fabricated from said second portion of said substrate having a thickness that is less than a thickness of the third portion of said substrate and with a width that is less than a width of the first portion of said substrate. In other embodiments, the sorptive material includes a microporous material, a chromatographic stationary phase, a getter, a sol-gel, or a polymer.

Additional exemplary micro preconcentrators, as well as structural components thereof, are described in U.S. Pat. Nos. 6,171,378 and 6,527,835, each of which is incorporated herein by reference in its entirety.

Opioid Compounds

Any useful analyte or compound can be detected using the system herein. In particular embodiments, the opioid compound is one that binds to one or more opioid receptors. In other embodiments, the opioid compound can be pyrolyzed to provide a characteristic backbone fragment.

Figure 3:
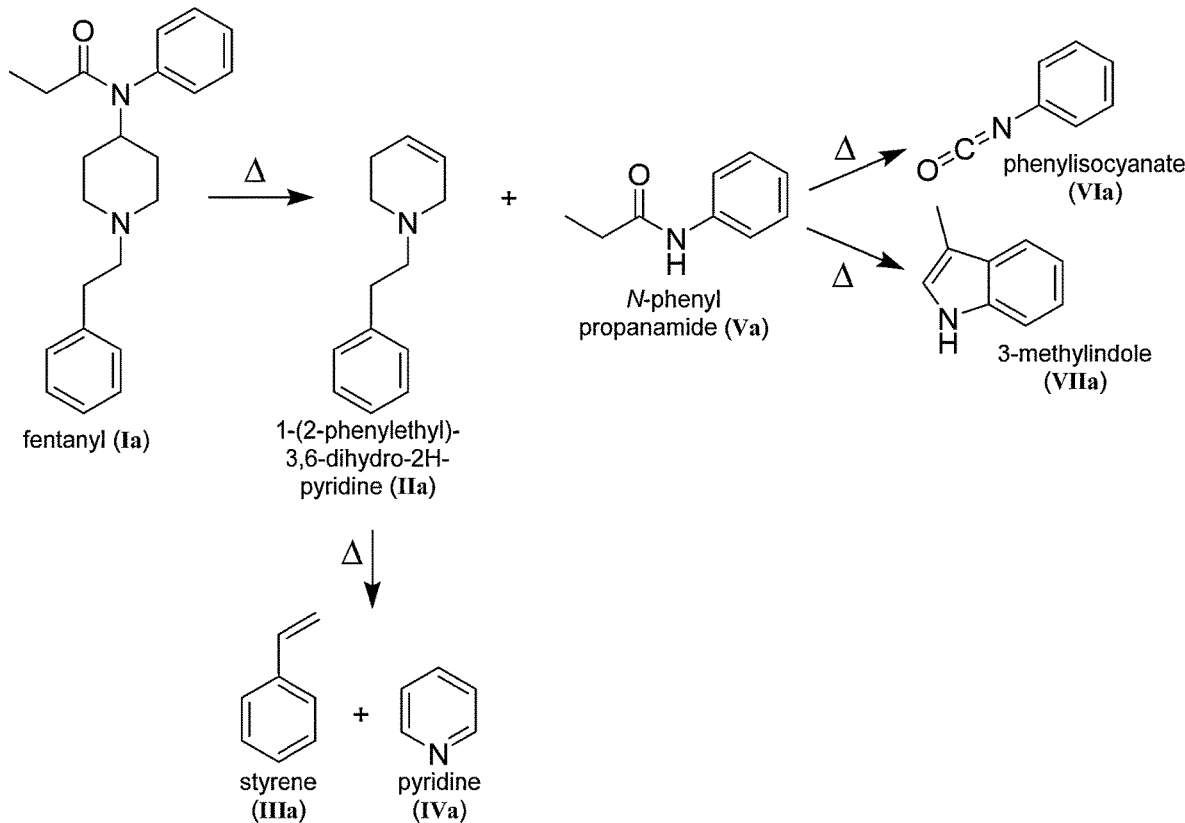
FIG. 3 provides an exemplary schematic showing pyrolysis of a fentanyl (compound Ia) into fragments (compounds IIa and Va), which can be further dissociated into smaller fragments (compounds IIIa, IVa, VIa, and VIIa).

FIG. 3 provides an exemplary schematic showing pyrolysis of a specific opioid compound, fentanyl (compound Ia). Upon pyrolysis (e.g., at an elevated temperature of about 500° C.), two fragments are formed: an exemplary backbone fragment (compound IIa) and another fragment (compound Va). These two fragments, in turn, can be exposed to further elevated temperatures (e.g., at an elevated temperature of about 750° C.) to provide secondary fragments: styrene (compound IIIa), pyridine (compound IVa), phenylisocyanate (compound VIa), and/or 3-methylindole (compound VIIa).

Figure 4:
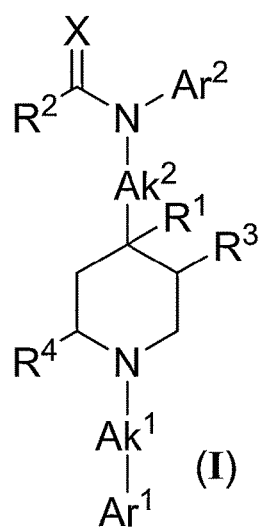
FIG. 4 provides a schematic of an exemplary opioid or opioid analogue (compound I) having substituents $R^1$, $R^2$, $R^3$, $R^4$, X, $Ak^1$, $Ak^2$, $Ar^1$, and $Ar^2$ (e.g., any substituents described herein).
Figure 5:
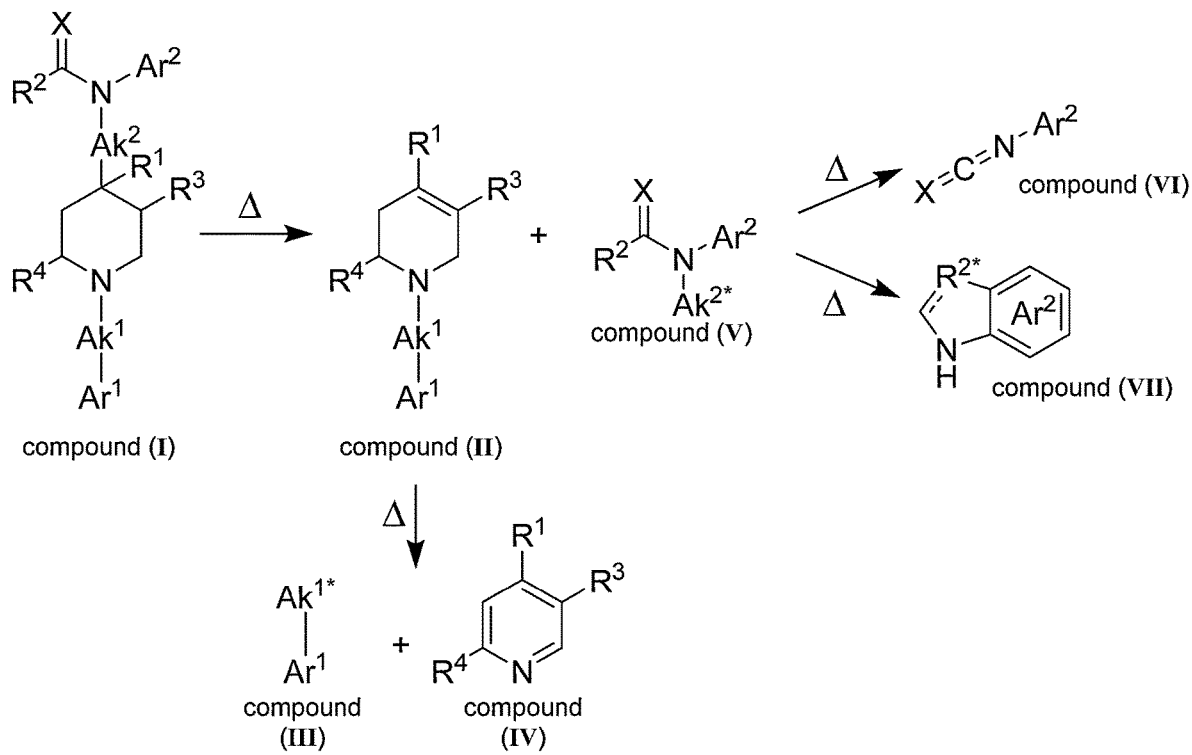
FIG. 5 provides an exemplary schematic showing pyrolysis of an opioid analogue (compound I) into fragments (compounds II and V), which can be further dissociated into smaller fragments (compounds III, IV, VI, and VII).

In addition to specific, known opioid compounds, pyrolysis can be employed on other potentially unknown opioid compounds or analogues. In particular embodiments, the compound is an opioid or an opioid analogue, such as compound (I) (FIG. 4) or a salt thereof. Pyrolysis of compound (I) can provide particular fragments, as seen in FIG. 5. In some embodiments, the backbone fragment has a structure of compound (II) or a salt thereof. In other embodiments, the fragment has a structure of compound (V) or a salt thereof. In yet other embodiments, one or more secondary fragments has a structure of compound (III), compound (IV), compound (VI), or compound (VII), or a salt thereof.

In particular embodiments, the compound is an opioid or an opioid analogue, such as compound (I) (FIG. 4):

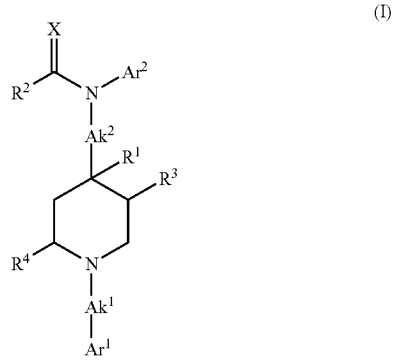

(I)

or a salt thereof, wherein:

$R^1$ is H, optionally substituted alkyl, optionally substituted alkoxyalkyl, optionally substituted alkoxycarbonyl, optionally substituted aryl, optionally substituted aryloxycarbonyl, or optionally substituted heterocyclyloxycarbonyl;

$R^2$ is H, optionally substituted alkyl, optionally substituted alkenyl, optionally substituted alkoxy, optionally substituted alkoxyalkyl, optionally substituted cycloalkyl, optionally substituted aryl, optionally substituted alkaryl, optionally substituted amino, optionally substituted heteroaryl, optionally substituted heterocyclyl, or optionally substituted alkheterocyclyl;

$R^3$ is H, optionally substituted alkyl, optionally substituted alkenyl, or halo;

$R^4$ is H or optionally substituted alkyl;

X is O or S;

$Ak^1$ is a bond, optionally substituted alkylene, optionally substituted heteroalkylene, optionally substituted alkyleneoxy, or optionally substituted cycloalkylene;

$Ak^2$ a bond, optionally substituted alkylene, or optionally substituted heteroalkylene;

$Ar^1$ is H, optionally substituted alkoxycarbonyl, optionally substituted aryl, optionally substituted aryloyl, optionally substituted aryloxycarbonyl, optionally substituted alkaryl, optionally substituted cycloalkyl, optionally substituted heteroaryl, optionally substituted heterocyclyl, or optionally substituted alkheterocyclyl; and $Ar^2$ is H, optionally substituted aryl, optionally substituted heteroaryl, or optionally substituted heterocyclyl, wherein $R^2$ and $Ar^2$, taken together, can be an optionally substituted heterocyclyl.

In some embodiments, $R^2$ is not H. In some embodiments, $Ar^1$ is not H. In other embodiments, $Ar^2$ is not H. In particular embodiments, each of $Ar^1$ and $Ar^2$ is, independently, an optionally substituted aryl. In some embodiments, $Ak^2$ is a bond.

In some embodiments, $R^1$ is H, optionally substituted alkyl, optionally substituted alkoxyalkyl (e.g., optionally substituted $C_{1-6}$ alkoxy-$C_{1-6}$ alkyl), optionally substituted alkoxycarbonyl (e.g., —C(O)—$OR^{T1}$, where $R^{T1}$ is optionally substituted $C_{1-12}$ alkyl, optionally substituted $C_{3-24}$ cycloalkyl, or optionally substituted heterocyclyl), optionally substituted aryl (e.g., optionally substituted phenyl), optionally substituted aryloxycarbonyl, or optionally substituted heterocyclyloxycarbonyl.

In some embodiments, $R^2$ is H, optionally substituted alkyl (e.g., optionally substituted $C_{1-6}$ or $C_{1-12}$ alkyl, including linear and branched alkyl), optionally substituted alkenyl (e.g., optionally substituted $C_{2-6}$ or $C_{2-12}$ alkenyl, including linear and branched alkyl), optionally substituted alkoxy (e.g., optionally substituted $C_{1-6}$ alkoxy), optionally substituted alkoxyalkyl (e.g., optionally substituted $C_{1-6}$ alkoxy-$C_{1-6}$ alkyl), optionally substituted cycloalkyl (e.g., optionally substituted $C_{3-24}$ cycloalkyl), optionally substituted aryl (e.g., optionally substituted phenyl), optionally substituted alkaryl (e.g., optionally substituted $C_{1-6}$ alk-$C_{4-18}$ aryl), optionally substituted amino (e.g., dialkylamino), optionally substituted heteroaryl, optionally substituted heterocyclyl (e.g., optionally substituted benzodioxolyl, furanyl, naphthalenyl, tetrahydrofuranyl, pyrrolidyl, morpholino, or piperidyl), or optionally substituted alkheterocyclyl.

In some embodiments, $R^3$ is H, optionally substituted alkyl (e.g., optionally substituted $C_{1-6}$ or $C_{1-12}$ alkyl), optionally substituted alkenyl (e.g., optionally substituted $C_{2-6}$ or $C_{2-12}$ alkenyl, including linear and branched alkyl), or halo.

In some embodiments, $R^4$ is H or optionally substituted alkyl (e.g., optionally substituted $C_{1-6}$ or $C_{1-12}$ alkyl).

In some embodiments, X is O or S.

In some embodiments, $Ak^1$ is a bond, optionally substituted alkylene (e.g., optionally substituted $C_{1-6}$ or $C_{1-12}$ alkylene, in which optionally substitutions can include, without limitation, one, two, three, or more of alkyl, hydroxyl, alkoxy, and/or halo), optionally substituted heteroalkylene, optionally substituted alkyleneoxy, or optionally substituted cycloalkylene.

In some embodiments, $Ak^2$ is a bond, optionally substituted alkylene, or optionally substituted heteroalkylene.

In some embodiments, $Ar^1$ is H, optionally substituted alkoxycarbonyl (e.g., —C(O)—$OR^{T1}$ where $R^{T1}$ is optionally substituted $C_{1-12}$ alkyl, optionally substituted $C_{3-24}$ cycloalkyl, or optionally substituted heterocyclyl), optionally substituted aryl (e.g., optionally substituted phenyl, in which optionally substitutions can include, without limitation, one, two, three, or more of alkyl, hydroxyl, alkoxy, halo, amino, and/or nitro), optionally substituted aryloyl, optionally substituted aryloxycarbonyl, optionally substituted alkaryl, optionally substituted cycloalkyl, optionally substituted heteroaryl, optionally substituted heterocyclyl (e.g., optionally substituted furanyl, furyl, oxotetrazolyl, piperidinyl, pyridyl, tetrahydrofuranyl, tetrazolyl, or thienyl), or optionally substituted alkheterocyclyl.

In some embodiments, $Ar^2$ is H, optionally substituted aryl (e.g., optionally substituted phenyl, in which optionally substitutions can include, without limitation, one, two, three, or more of alkyl, hydroxyl, alkoxy, halo, amino, and/or nitro), optionally substituted heteroaryl, or optionally substituted heterocyclyl (e.g., optionally substituted pyrazinyl or pyrrolyl).

Figure 6A:
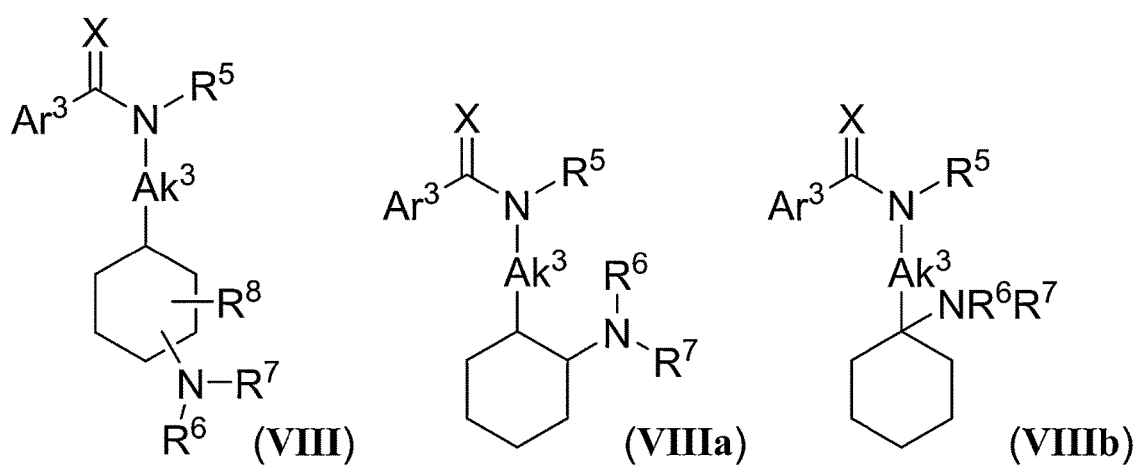
FIGS. 6A-6B provide (A) a schematic of an exemplary opioid analogue (compound VIII, VIIIa, or VIIIb) having substituents $R^5$, $R^6$, $R^7$, $R^8$, X, $Ak^3$, and $Ar^3$ (e.g., any substituents described herein) and (B) an exemplary schematic showing pyrolysis of an opioid analogue (compound VIII) into fragments (compounds X and XII), which can be further dissociated into smaller fragments (compounds XI, XIII, and XIV).
Figure 6B:
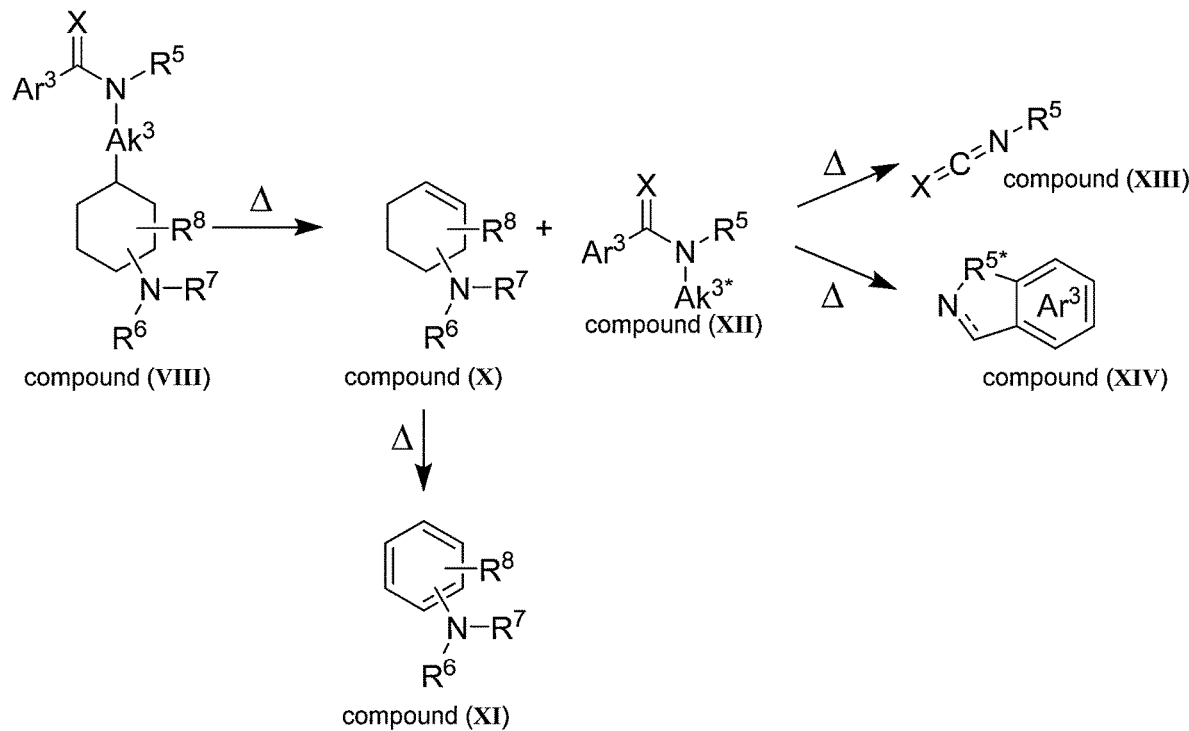
Figure 7:
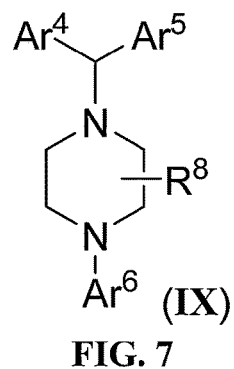
FIG. 7 provides a schematic of an exemplary opioid analogue (compound IX) having substituents $R^8$, $Ar^4$, $Ar^5$, and $Ar^6$ (e.g., any substituents described herein).

Furthermore, pyrolysis can be performed on synthetic opioid compounds or synthetic opioid analogues. In particular embodiments, the compound is an opioid or an opioid analogue, such as compound (VIII), compound (VIIIa), or compound (VIIIb) (FIG. 6A) or a salt thereof, as well as compound (IX) (FIG. 7) or a salt thereof. Pyrolysis of compound (VIII) can provide particular fragments, as seen in FIG. 6B. In some embodiments, the backbone fragment has a structure of compound (X) or a salt thereof. In other embodiments, the fragment has a structure of compound (XII) or a salt thereof. In yet other embodiments, one or more secondary fragments has a structure of compound (XI), compound (XIII), or compound (XIV), or a salt thereof.

In particular embodiments, the compound is an opioid or an opioid analogue, such as compound (VIII), (VIIIa), or (VIIIb):

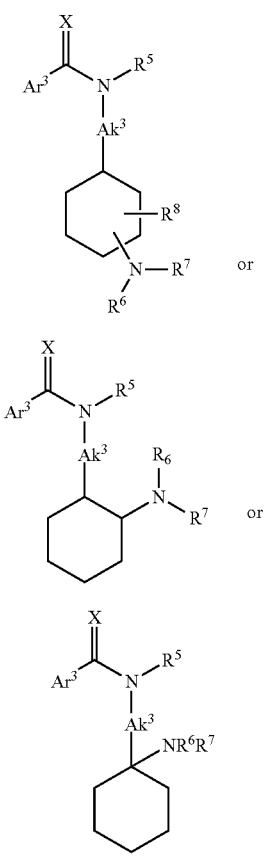

or a salt thereof, wherein:
each of $R^5$, $R^6$, and $R^7$ is, independently, H or optionally substituted alkyl, wherein $R^6$ and $R^7$, taken together, can be an optionally substituted heterocyclyl;
$R^8$ is H, optionally substituted alkyl, optionally substituted heteroalkyl, optionally substituted alkoxy, optionally substituted spirocyclyl, halo, hydroxyl, optionally substituted aryl, optionally substituted alkaryl, optionally substituted heterocyclyl, or optionally substituted alkheterocyclyl;
X is O or S;

$Ak^3$ is a bond, optionally substituted alkylene, or optionally substituted heteroalkylene; and
$Ar^3$ is H, optionally substituted aryl (e.g., optionally substituted phenyl or optionally substituted naphthalenyl, in which optionally substitutions can include, without limitation, one, two, three, or more of alkyl, hydroxyl, alkoxy, halo, amino, and/or nitro), optionally substituted alkaryl, optionally substituted heteroaryl, optionally substituted heterocyclyl, or optionally substituted alkheterocyclyl.

In yet other embodiments, the compound is an opioid or an opioid analogue, such as compound (IX):

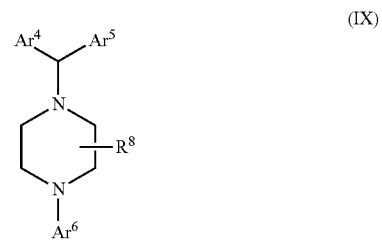

or a salt thereof, wherein:
$R^8$ is H, optionally substituted alkyl, optionally substituted heteroalkyl, optionally substituted alkoxy, optionally substituted spirocyclyl, halo, hydroxyl, optionally substituted aryl, optionally substituted alkaryl, optionally substituted heterocyclyl, or optionally substituted alkheterocyclyl;
each of $Ar^4$ and $Ar^5$ is, independently, optionally substituted aryl, optionally substituted alkaryl, optionally substituted cycloalkyl, optionally substituted heteroaryl, optionally substituted heterocyclyl, or optionally substituted alkheterocyclyl; and
$Ar^6$ is H, optionally substituted alkyl, optionally substituted alkenyl, optionally substituted aryl, optionally substituted alkaryl, optionally substituted cycloalkyl, optionally substituted heteroaryl, optionally substituted heterocyclyl, or optionally substituted alkheterocyclyl.

In some embodiments, $A^5$ is optionally substituted alkaryl or optionally substituted alkheterocyclyl. In other embodiments, $Ar^4$ and is optionally substituted aryl, optionally substituted cycloalkyl, optionally substituted heteroaryl, or optionally substituted heterocyclyl (e.g., optionally substituted furanyl, furyl, oxotetrazolyl, piperidinyl, pyridyl, tetrahydrofuranyl, tetrazolyl, or thienyl).

Yet other exemplary compounds (e.g., target compounds) include an opiate, an opioid, an opiate intermediate, a Schedule I opiate, a Schedule II opiate, or a compound from WO2007093603, which is incorporated herein by reference in its entirety. Additional compounds can include fentanyl, acetylfentanyl, acetyl-α-methylfentanyl, acrylfentanyl, acryl-α-methylfentanyl, acryloylfentanyl, AD-1211 (1-(3-methyl-2-butenyl)-4-[(1R)-1-phenyl-2-(3-hydroxyphenyl) ethyl]piperazine), AH-7921 (3,4-dichloro-N-{[1-(dimethylamino) cyclohexyl]methyl}benzamide), alfentanil, 3-allylfentanyl, anileridine, 4-anilino-N-phenethyl-4-piperidine, benzodioxolefentanyl, benzoylfentanyl, benzylfentanyl, brifentanil, brorphine, butyrylfentanyl, 3-carbomethoxyfentanyl, carfentanil, p-chlorofuranylfentanyl, 4-chloroisobutyrylfentanyl, cyclopropylfentanyl, cyclobutylfentanyl, cyclopentylfentanyl, cyclohexylfentanyl, despropionyl fentanyl, 2,2'-difluorofentanyl, 2,5-dimethylfentanyl, EAZ-91-05 ((quinuclidin-3-yl) 4-[phenyl (propanoyl)amino]-1-[2-(indol-3-yl)ethyl]piperidine-4-carboxylate), fentanyl 4-methylene analogue (N-phenyl-N-

{[1-(2-phenylethyl)piperidin-4-yl]methyl}propanamide), fentanyl N-oxide, 4-fluorobutyrylfentanyl, 4-fluoroisobutyrylfentanyl, m-fluorofentanyl, o-fluorofentanyl, p-fluorofentanyl, 3-fluorofentanyl, 4-fluorofentanyl, p-fluorofuranylfentanyl, p-fluoroisobutyrylbenzylfentanyl, furanylethylfentanyl, furanylfentanyl, Höchtanyl (N-[1-(2-phenylethyl)piperidin-4-yl]-N-pyrrol-1-ylpropanamide), homofentanyl (N-phenylpropylnorfentanyl), hybrid of fentanyl & haloperidol (N-phenyl-N-{1-[4-(4-fluorophenyl)-4-oxobutyl]piperidin-4-yl}propanamide), p-hydroxyfentanyl, O-hydroxy-3-methylfentanyl, β-hydroxy-4-methylfentanyl, 4-hydroxy-N-phenethylpiperidine, p-hydroxy-thiofentanyl, isobutyrylfentanyl, isofentanyl, o-isopropylfuranylfentanyl, lofentanil, methoxyacetylfentanyl, 4-methoxyburtyrylfentanyl, o-methoxyfuranylfentanyl, α-methylacetylfentanyl, 3-methylbutyrylfentanyl, α-methylbutyrylfentanyl, α-methyl-ρ-hydroxyfentanyl, α-methylfentanyl (α-mefentanyl), β-methylfentanyl, 3-methylfentanyl (mefentanyl), (+)-cis-3-methylfentanyl, (+)-trans-3-methylfentanyl, 3-methylfuranylfentanyl, 3-methylindole, N-methylnorcarfentanyl, 4-methylphenethylacetylfentanyl, α-methylthiofentanyl, 3-methylthiofentanyl, mirfentanil, MT-45 (1-cyclohexyl-4-(1,2-diphenylethyl)piperazine), noralfentanil, norfentanyl, norsufentanil, ocfentanil, ohmefentanyl, phenaridine, 1-phenethyl-1H-pyridin-2-one, phenethylpiperidene, phenethylpiperidiene, phenethylpyridinium salt, N-phenethyl-1,2,5,6-tetrahydropyridine, N-cyanoethyl-1,2,5,6-tetrahydropyridine, N-phenoxyethyl-1,2,5,6-tetrahydropyridine, N-propyl-1,2,5,6-tetrahydropyridine, N-phenylmethyl-1,2,5,6-tetrahydropyridine, N-phenyl-1-(2-phenylethyl)piperidin-4-amine, trans-phenylcyclopropyl-norfentanyl, N-phenyl-N-[1-(2-cyanoethyl)piperidin-4-yl] propanamide, N-phenyl-N-[1-(2-phenoxyethyl)piperidin-4-yl]propanamide, N-phenyl-N-[1-(2-phenylmethyl) piperidin-4-yl]propanamide, N-phenyl-N-[1-(2-propyl) piperidin-4-yl]propanamide, 4-phenylfentanyl, phenylisocyanate, N-phenylpropanamide, 3-phenylpropanoylfentanyl, N-[1-(β-phenylethyl)-4-piperidyl]butyranilide, N-[1-(β-phenylethyl)-4-piperidyl]propionanilide, N-[1-(β-phenylethyl)-4-piperidyl]-o-propionotoluidide, N-[1-(α-methyl-ρ-phenylethyl)-4-piperidyl]propionanilide, N-[1-(β-thienylethyl)-4-piperidyl]propionanilide, N-[1-(β-furylethyl)-4-piperidyl]propionanilide, N-[1-(β-phenylethyl)-4-piperidyl]-N-phenylpropanecarboxamide, N-[1-(β-phenylethyl)-4-butyl-4-piperidyl]propionanilide, N-[1-(β-cyclohexylethyl)-4-piperidyl]propionanilide, N-[1-(3-cyclohexylethyl)-4-piperidyl]-N-phenylcyclopropanecarboxamide, propionanilide, pyridin-4-ylethyl-norfentanyl, pyruvylfentanyl, R-30490 (N-[4-(methoxymethyl)-1-(β-phenylethyl)piperidin-4-yl]-N-phenylpropanamide), remifentanil, secofentanyl, spiradoline, 1-styryl-1H-pyridin-2-one, sufentanil, tetrahydrofuranylfentanyl, 2,2,3,3,-tetramethylcyclopropylfentanyl, thenylfentanyl, thiafentanil, thienylfentanyl, thiofentanyl, trefentanil, trifluorofentanyl, U-47700 (3,4-dichloro-N-[(1R,2R)-2-(dimethylamino)cyclohexyl]-N-methylbenzamide), U-48800 (3,4-dichloro-N-[(1R,2R)-2-(dimethylamino)cyclohexyl]-N-methylbenzamide), U-49900 (3,4-dichloro-N-(2-(diethylamino)cyclohexyl)—N-methylbenzamide), U-50488 (2-(3,4-dichlorophenyl)-N-methyl-N-[(1R,2R)-2-pyrrolidin-1-ylcyclohexyl]acetamide), U-51754 (trans-3,4-dichloro-N-[2-(dimethylamino) cyclohexyl]-N-methyl-benzeneacetamide), U-69593 (N-methyl-2-phenyl-N-[(5R,7S,8S)-7-(pyrrolidin-1-yl)-1-oxaspiro[4.5]dec-8-yl]acetamide), and valerylfentanyl, as well as salts thereof and isomers thereof. Additional opioid compounds are described in Breindahl T et al., "Identification of a new psychoactive substance in seized material: the synthetic opioid N-phenyl-N-[1-(2-phenethyl)piperidin-4-yl]prop-2-enamide (acrylfentanyl)," Drug Test. Analysis 2017; 9:415-22; Garg A et al., "Forced degradation of fentanyl: identification and analysis of impurities and degradants," J. Pharm. Biomed. Analysis 2010; 53:325-34; Manral L et al., "Thermal behaviour of fentanyl and its analogues during flash pyrolysis," J. Thermal Analysis Calorimetry 2009; 96:531-4; Nishikawa R K et al., "Potential biomarkers of smoked fentanyl utilizing pyrolysis gas chromatography-mass spectrometry," J. Anal. Toxicol. 2009; 33:418-22; Skulska A et al., "Fentanyl and its analogues in the forensic laboratory: medical and analytical problems," Problems Forensic Sci. 2004; 59:127-42; Valdez C A et al., "Analysis of chemical warfare agents by gas chromatography-mass spectrometry: methods for their direct detection and derivatization approaches for the analysis of their degradation products," Rev. Anal. Chem. 2018; 20170007 (26 pp.); Vandergrift G W et al., "Paper spray mass spectrometry for the direct, semi-quantitative measurement of fentanyl and norfentanyl in complex matrices," Clin. Biochem. 2018; 54:106-11; Verkouteren J R et al., "Reliability of ion mobility spectrometry for qualitative analysis of complex, multicomponent illicit drug samples," Forensic Sci. Int'l 2011; 206:190-6; and U.S. Pat. No. 3,164,600, each of which is incorporated herein by reference in its entirety.

EXAMPLES

Example 1: Synthetic Opioid Detection Technology

Described herein is detector design to simplify the synthetic opioid detection challenge by using a unique pyrolysis-based detection method. In particular, our proposed effort aims to significantly simplify the synthetic opioid detection challenge, of which fentanyl is the most commonly-known compound, by using a unique pyrolysis-based detection method. Pyrolysis has been demonstrated in the literature to thermally fragment synthetic opioid compounds, and gas chromatograph-mass spectrometer (GC-MS) can be employed to detect such fragments (see, e.g., Manral L et al., "Thermal behaviour of fentanyl and its analogues during flash pyrolysis," J. ThermalAnalysis Calorimetry 2009; 96(2):531-4). In addition, ion mobility spectrometry (IMS) has been proven to detect synthetic opioids (see, e.g., Verkouteren J R et al., "Reliability of ion mobility spectrometry for qualitative analysis of complex, multicomponent illicit drug samples," Forensic Sci. Internat'l 2011; 206:190-6).

Evidence indicates that a single, repeatable pyrolysis fragment (e.g., N-phenylpropanamide, compound Va) was common amongst fentanyl and five of its tested analogues, as well as secondary fragments that may provide additional chemical information useful for identification. In some instances, as seen in FIG. 3, exposure of fentanyl (compound Ia) to an increased temperature (e.g., about 500° C.) produces N-phenylpropanamide (compound Va) (an exemplary backbone fragment) and phenethylpiperidene (compound IIa). Upon exposure to further elevated temperatures (e.g., about 750° C.) can produce secondary or daughter fragments, such as pyrolysis of compound IIa to secondary fragments (e.g., styrene (compound IIIa) and pyridine (compound IVa)), as well as pyrolysis of compound Va to other secondary fragments (e.g., phenylisocyanate (compound VIa) and 3-methylindole (compound VIIa)). Such secondary fragments can assist in specifically identifying the structure of the analogue.

This approach represents an opportunity to construct a portable detection system for synthetic opioid compounds independent of their analogue. In particular, we propose to study the detection of this backbone fragment with IMS by studying its ion-molecule adduct pathways and drift behaviors.

Current detection technologies cannot recognize unknown opioid analogues. Synthetic opioid compounds pose a unique detection challenge because producers can rapidly proliferate chemical structure alterations, or analogues, of the basic molecule to increase drug potency and circumvent drug detection technologies. This means detector libraries, whether on IMS or mass spectrometer (MS) systems, must be updated in the field to account for the discovery of new analogues, as otherwise unknown analogues will remain undetectable. While notionally simple, the actual library update process is time-consuming, error prone, and may lead to increased false alarm rates as the new target analytes introduce a new range of possible environmental interferents that could be detected instead. While literature reports approximately 1,400 possible fentanyl analogues, only about 200 specific formulations have been synthesized or studied, and most commercial detector technologies are capable of reporting only a few (<10) of those.

To our knowledge, synthetic opioid pyrolysis has not been used as a detection method for this class of compounds before. Sandia has developed a suite of sensor technologies, including thermal preconcentrators and micro gas chromatography columns that could enable a portable detection system that transitions this prior literature observation into a fieldable, portable system with extremely low false alarm rates. This approach is highly amenable to portable instrumentation, as Sandia has developed a variety of microhotplate structures (e.g., pyrolyzers) that are capable of the rapid (e.g., 10's of msec) temperature ramps to high temperature (e.g., ~500° C.) necessary to decompose the target compounds into useful fragments by pyrolysis. Slow (e.g., 1-2 minute), low temperature (e.g., ~300° C.) thermal decomposition has been demonstrated in the literature as well, but these studies seem less promising because they produce a larger number of potential target fragments that increases the detection challenge. Without wishing to be limited to this particular embodiment, we hypothesize that these pyrolysis fragments, especially this N-phenylpropanamide backbone fragment, will be detectable with IMS detectors. This would allow for the creation of a novel, portable sensor architecture able to natively detect the approximately thousands of possible opioid compounds with an extremely low false alarm rate.

In one non-limiting embodiment, combining technical components (e.g., microhotplate, micro gas chromatography (GC), and IMS detector technologies) into an integrated system is expected to produce a field portable detector with a low parts per billion to parts per trillion sensitivity and an extremely low false alarm rate. Additional details follow.

Example 2: Thermal Decomposition of Chemical Analogues as a Low-False Alarm Rate Method for Detection of Classes of Chemical Compounds We have demonstrated a pyrolysis-based technique that can be used, as part of an analytical system, to enable the detection of broad classes or families of chemical compounds. There are a wide variety of substances of interest, such as synthetic opioids, cannabinoids, and some chemical warfare agents, that are chemical analogues of one another. While it is ideal to identify the specific analogue, at times, due to the limitations of detector technology (especially portable detectors), it may be sufficient (and actionable) to simply identify the target compound as belonging to a wider class, e.g. fentanyl compounds.

Chemical analogues can be thermally-decomposed or pyrolyzed into repeatable chemical fragments ("daughter" fragments) that can be used to characteristically identify a chemical family. Pyrolysis is a historical analytical chemistry technique that is amenable to portable detector systems as it requires minimal sample prep and it produces volatile compounds for analysis-enabling solids, liquids, and gasses to be studied. While thermal decomposition of chemical compounds has been studied for academic and commercial applications, no other group has recognized the technique's use to characterize large analogue families and circumvent the limitations of traditional library-based detection approaches.

We have shown that by varying the rate of a thermal ramps, atmospheric composition, and the maximum temperature of pyrolysis that we can produce a varying array of pyrolyzed daughter fragments. Some of the fragments produced are non-selective and could be produced by other environmental sources, while others are highly selective towards specific analogue families. The maximum temperature of the pyrolysis step is related to the thermal robustness of the chemical family, but can easily exceed 500° C. Ramp rates can vary from 10's of ° C. per second to 10's of ° C. per msec. The presence of oxygen in the environment during decomposition changes the character of the daughter fragments as well, and we have demonstrated that the production of certain daughter fragments can be completely suppressed by adding or removing oxygen. In the same way, dopants or catalysts could be used to enhance or reduce the production of certain fragments.

We have shown that a few representative chemicals from the analogue family can be studied to understand the daughter fragmentation process. Once fragmentation studies are undertaken, potential daughter fragment targets can be identified based on their production efficiency, their selectivity toward the target class, and their amenability to detection. Once these key daughter fragments are identified, we can modify the thermal and atmospheric variables mentioned above to maximize production of these key fragments.

One exemplar of the technique is the identification of analogues from the fentanyl family of synthetic opioids. We have demonstrated that thermally-decomposing fentanyl and its analogues produces a family of reoccurring daughter products that include N-phenyl propanamide (NPP or compound Va), styrene (compound IIIa), and pyridine (compound IVa). Of these, compounds like styrene and pyridine are non-selective towards synthetic opioids and thus could easily lead to false positive detection events as they are produced by a variety of sources. NPP, however, is a selective fragment not found in abundance outside of the manufacture of synthetic opioids. This fragment appears when a fentanyl analogue is properly pyrolyzed in air at slower (e.g., 10's of ° C./sec) ramp rates. Production of NPP fragments has been found in all fentanyl analogues tested, though variations exist between the analogues regarding the production efficiency of the NPP fragment. These variations in conversion efficiency are based on the molecular structure of the analogue, but due to the high temperatures encountered during pyrolysis, molecular fragments readily react and reconfigure themselves to energetically stable structures. These energetically-stable structures make the ideal target daughter fragments.

The power of the technique, illustrated by our exemplar, lies in the fact that there are possibly tens of thousands of fentanyl analogues that can be synthesized. Library-based detection techniques, like mass spectrometry (MS) and ion-mobility spectrometry (IMS) must uniquely characterize each target compound to detect them. A library database entry might consist of the gas chromatography separation time of the analogue and the MS fragmentation pattern (which typically consist of dozens of fragments) or the characteristic drift time (for an IMS detector) of the analogue. With our proposed approach, we can use a few target fragments, like NPP, as markers for the entire compound class and thus could identify both known and unknown chemicals within the family. The 2017 NIST MS database currently has only ~30 fentanyl analogues characterized, and with the number of potential analogues available it would require significant investment of time and resources to synthesize and characterize all of them for inclusion into detection libraries. Additionally, even if all these compounds could be characterized, for a system with insufficient analytical resolution such as portable detection systems, this large number of library entries would increase the false alarm rate of the system such that it was unusable. The reason for this is that, as the detection library grows, the number of possible interferents that could initiate a detection alarm grows as well. By using this technique, we can reduce the library database entries for the entire fentanyl chemical family by orders of magnitude and thus greatly reduce our false alarm rate in a portable system.

Sandia has designed a variety of platforms, both microfabricated and conventionally-fabricated, that are suitable for thermal decomposition of analytical samples. Microfabricated collection structures capable of acting as thermal decomposition platforms include planar silicon nitride membranes with integrated heater wiring, as well as three-dimensional etched silicon structures with integrated heaters. These 3D structures are particularly effective at analyte capture and decomposition as they provide a high-surface area and a tortuous flow path that increases the interaction probability between a heated surface and the target analyte. Exemplary micro pyrolyzer structures are provided in FIGS. 2C-2D.

Conventional structures capable of analyte thermal decomposition include metal meshes and metal foams with a high surface area for chemical capture. Non-limiting examples of these later designs include the metal meshes used for explosives capture employed by the MicroHound and PocketPup collector/preconcentrator systems. The microfabricated or conventionally-fabricated collectors can be loaded with sample by a variety of methods, such as by an air sampling pump that draws gas flow through the collector or by swipes or swabs.

To thermally decompose a sample, the front-end that contains the captured material can rapidly achieve an elevated temperature to assure preferential molecular decomposition pathways. Fentanyl, for example, is stable up to 350° C. and so a front-end able to survive at least a brief, 10's-1000's of msec, excursions to this temperature is required. For the fentanyl family of compounds, a collection platform able to exceed about 700° C. is ideal as several daughter fragments are only produced at these elevated temperatures.

Once the pyrolyzed fragments are produced, they can be drawn into a microfabricated GC column that will separate the fragments in time. The advantage of this separation step is that the number of compounds introduced to the detector per unit time is reduced, meaning there is a lower chance for a detector to false alarm or mischaracterize a chemical target. Additionally, the information gained from the fragment's elution time can also be used to help uniquely identify the fragment.

The detector can include an IMS system. In particular embodiments, the IMS detector uses unique algorithms to increase the detection sensitivity and reject system noise. It can also detect both positive or negative ions, which could be used to further reject potential interferents.

Overall, such a portable system would be ~4 lbs in weight and could operate on battery power for a 4-6 hr mission to detect target compound families in the field. For several applications, such as the detection of synthetic opioids, this could provide the ability to detect both known and unknown analogues, which is a capability that no other detection system has. Future uses of this technique and the proposed sensing system include detection of other drugs of abuse such as synthetic cannabinoids.

Example 3: Fragmentation Studies Using IMS Detection

Analytical studies will be conducted to study the pyrolysis decomposition of a wide range of synthetic opioids at different temperatures and atmospheres. Such studies could identify backbone fragments and resulting daughter fragments, in which resulting fragmentation patterns can then be correlated to the original opioid compound being tested. Any useful instrumentation can be employed, such as a pyrolyzer sample inlet followed by two-dimensional gas chromatography separation and a time of flight mass spectrometer as a detector (PY-GCxGC-TOFMS).

Once the key backbone and daughter fragments are identified, further studies can focus on understanding the behavior of these fragments within an IMS detector. In use, incoming chemicals are ionized, thereby forming adducts that include the target ion and one or more other chemical species. Characteristic elution speed, called a reduced mobility value or $K_0$, of the parent ion and these adducts can positively identify the target species. Mass to charge ratio (m/z) values for the parent ion, adducts, or other formed species can identify opioid compounds as well. Thus, studies can include understanding the ion-molecular interactions of pyrolysis fragment by determining characteristic $K_0$ and/or m/z values.

In one non-limiting instance, ion mobility-mass spectrometry (IMS/MS) can be employed to probe the molecular shape and structure of the N-phenylpropanamide ion-molecule adduct. For instance, this backbone ion fragment can be exposed to a variety of ion adduct forming species (e.g., $NH_4^+$, $CH_2O_2^+$, etc.) and then investigate $K_0$ and m/z values for the species formed. Differing ion adduct forming species can be employed to explore different aspects of gas-phase ion chemistry using IMS.

Other experiments can employ different drift gas. In one instance, we will ionize N-phenylpropanamide in the presence of drift, or dopant, gas modifiers (e.g., nicotinamide, $NH_4^+$) and without drift gas modifier and will compare the resulting $K_0$ values. Yet other experiments can investigate the charge of pyrolysis fragments (e.g., either positive or negative charge). Negative mode ionization can be helpful to reduce potential false positives from other interfering compounds that may have similar mobility values.

Example 4: Development of the Architecture for a Portable Detection System

Various components can be combined to provide a portable detection system. Such components can include, e.g., one or more micro pyrolyzers, one or more micro gas chromatograph (pGC) technologies, and/or one or more micro detectors (e.g., a miniature ion mobility spectrometer (IMS)). Combining such technical components can be provided in any useful architecture, e.g., such as within an integrated system.

In one non-limiting instance, the micro pyrolyzer includes a planar silicon nitride membrane with integrated heater wiring or a three-dimensional etched silicon structure with integrated heaters.

In another non-limiting instance, the pGC includes a silicon pGC column with optional integrated metal heaters for separation of low volatility compounds.

In yet another non-limiting instance, the detector is a miniaturized low-temperature co-fire ceramic (LTCC) IMS using an Am241 (20uCi) source for ionization (see, e.g., KB Pfeifer et al., "Measurement of ion swarm distribution functions in miniature low-temperature co-fired ceramic ion mobility spectrometer drift tubes," Anal. Chem. 2005; 77:5215-20; and KB Pfeifer et al., "Signal-to-noise and resolution enhancement in ion mobility spectrometry using correlation gating techniques: Barker codes," IEEE Sensors J. 2007; 7:1130-7). IMS signals can be processed in any useful manner, such as by employing a correlation IMS (CIMS) technique that applies pulse compression to IMS signals, thereby achieving high signal-to-noise and higher resolution over conventional approaches. In another non-limiting instance, the detector is a surface acoustic wave (SAW) detector (see, e.g., FIG. 2B).

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of detecting an opioid compound comprising:
capturing an opioid compound on a metal mesh comprising a surface area for chemical capture, wherein the metal mesh is provided in a front-end;
thermally decomposing the captured material on the metal mesh at an elevated temperature of from about 500° C. to about 900° C. to produce a plurality of backbone fragments indicative of a compound being in an opioid class;
further thermally decomposing the plurality of backbone fragments at a further elevated temperature greater than said elevated temperature to produce a plurality of secondary fragments indicative of a structure of the compound;
capturing and separating the plurality of backbone fragments and secondary fragments in a micro gas chromatograph comprising a micro gas chromatograph column and a stationary phase disposed on a surface of the micro gas chromatograph column, wherein the stationary phase is configured to interact with the plurality of backbone fragments and secondary fragments; and
eluting the plurality of backbone fragments and secondary fragments from the micro gas chromatograph column to a micro detector, wherein the micro detector is configured to detect the presence of the plurality of backbone fragments and secondary fragments.

2. The method of claim 1, further comprising:
delivering the plurality of backbone fragments and secondary fragments to the micro gas chromatograph column by use of a carrier gas.

3. The method of claim 1, wherein the opioid compound has a structure of formula (I) or a salt thereof.

4. The method of claim 3, wherein at least one of the plurality of backbone fragments has a structure of formula (II) or a salt thereof.

5. The method of claim 1, wherein the opioid compound has a structure of formula (VIII), (VIIIa), (VIIIb), or (IX) or a salt thereof.

6. The method of claim 5, wherein at least one of the plurality of backbone fragments has a structure of formula (X) or a salt thereof.

7. The method of claim 3, wherein at least one of the plurality of secondary fragments has a structure of formula (III), (IV), (VI), (VII), or a salt thereof.

8. The method of claim 5, wherein at least one of the plurality of secondary fragments has a structure of formula (XI), (XIII), (XIV), or a salt thereof.

\* \* \* \* \*